United States Patent
Fu et al.

(10) Patent No.: US 11,578,053 B2
(45) Date of Patent: Feb. 14, 2023

(54) CHEMICAL PROCESS FOR PREPARING PHENYLPIPERIDINYL INDOLE DERIVATIVES

(71) Applicant: NOVARTIS AG, Basel (CH)

(72) Inventors: Peng Fu, Suzhou (CN); Yu Gai, Shanghai (CN); Feng Gao, Shanghai (CN); Weiyong Kong, Suzhou (CN); Yadong Lu, Changshu (CN); Zhongcheng Min, Shouzhou (CN); Shaofeng Rong, Changshu (CN); Chutian Shu, Shanghai (CN); Can Wang, Suzhou (CN); Ruidong Wang, Shanghai (CN); Jibin Zhao, Suzhou (CN); Xianglin Zhao, Shanghai (CN); Yi Zhao, Xiangcheng (CN); Jianguang Zhou, Suzhou (CN); Benjamin Martin, Leymen (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 17/546,284

(22) Filed: Dec. 9, 2021

(65) Prior Publication Data
US 2022/0169630 A1    Jun. 2, 2022

Related U.S. Application Data

(63) Continuation of application No. 17/260,393, filed as application No. PCT/IB2019/056024 on Jul. 15, 2019, now Pat. No. 11,208,398.

(30) Foreign Application Priority Data

Jul. 16, 2018  (WO) ............... PCT/CN2018/095828

(51) Int. Cl.
| | | |
|---|---|---|
| C07D 401/06 | (2006.01) | |
| C07D 209/04 | (2006.01) | |
| C07D 211/74 | (2006.01) | |

(52) U.S. Cl.
CPC ......... *C07D 401/06* (2013.01); *C07D 209/04* (2013.01); *C07D 211/74* (2013.01)

(58) Field of Classification Search
CPC ... C07D 401/06; C07D 209/04; C07D 211/74
See application file for complete search history.

(56) References Cited

U.S. PATENT DOCUMENTS

| 9,682,968 | B2 | 6/2017 | Adams et al. |
| 11,208,398 | B2 * | 12/2021 | Fu ....................... C07D 209/04 |

FOREIGN PATENT DOCUMENTS

| EA | 201690223 A1 | 6/2016 |
| WO | 2004022057 A1 | 3/2004 |
| WO | 2014/143638 A1 | 9/2014 |
| WO | 2015/009616 A1 | 1/2015 |
| WO | 2018/134710 A1 | 7/2018 |

OTHER PUBLICATIONS

International Search Report issued from corresponding PCT/IB2019/056024, dated Jan. 23, 2020.

* cited by examiner

*Primary Examiner* — Timothy R Rozof
(74) *Attorney, Agent, or Firm* — Francine F. Li

(57) ABSTRACT

The present invention relates to a method of synthesizing a compound of formula (I) also referred to as 4-(((2S,4S)-(4-ethoxy-1-(((5-methoxy-7-methyl-1H-indol-4-yl)methyl)piperidin-2-yl))benzoic acid, or a pharmaceutically acceptable salt thereof, and/or intermediates thereof, their use as pharmaceuticals and pharmaceutical compositions and the use of intermediates for preparing a compound of formula (I), or a pharmaceutically acceptable salt thereof.

10 Claims, 1 Drawing Sheet

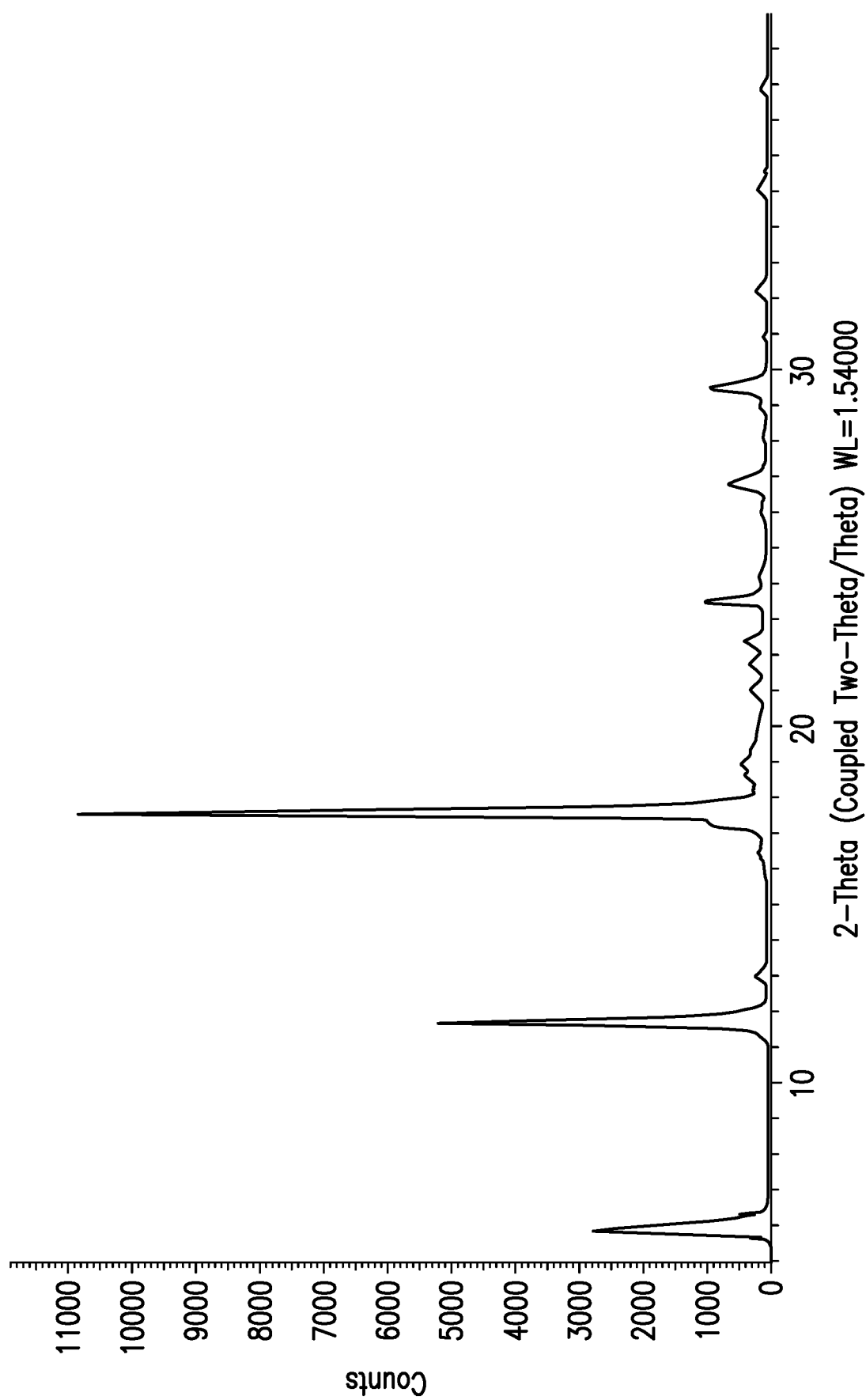

CHEMICAL PROCESS FOR PREPARING PHENYLPIPERIDINYL INDOLE DERIVATIVES

This is a continuation of U.S. application Ser. No. 17/260,393, filed on Jan. 14, 2021, which is a 371 of PCT/IB2019/056024, filed on Jul. 15, 2019, which claims benefit of Chinese Application No. PCT/CN2018/095828 filed on Jul. 16, 2018, the entire disclosures of which are hereby incorporated by reference.

FIELD OF THE INVENTION

The present invention relates to processes, process steps and intermediates useful in the preparation of phenylpiperidinyl indole derivatives. In particular, the present invention is in the field of organic synthesis and is directed to a method of synthesizing a compound of formula (I), also referred to as 4-((2S,4S)-(4-ethoxy-1-((5-methoxy-7-methyl-1H-indol-4-yl)methyl)piperidin-2-yl))benzoic acid, or a pharmaceutically acceptable salt thereof, and/or intermediates thereof, methods for further preparing pharmaceutical compositions of the compound of formula (I), or its intermediates, the use of intermediates for preparing a compound of formula (I) and the intermediates themselves.

BACKGROUND OF THE INVENTION

The present invention relates to a process for the preparation of phenylpiperidinyl indole derivatives. More particularly, the present invention relates to a process for the preparation of the compound of formula (I)

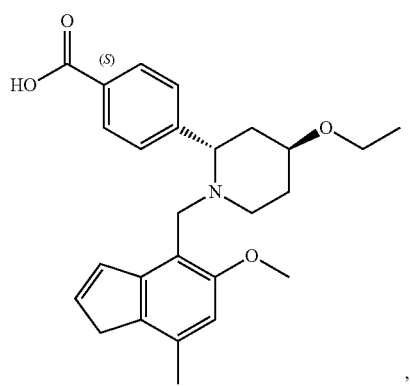

also referred to as 4-((2S,4S)-(4-ethoxy-1-((5-methoxy-7-methyl-1H-indol-4-yl)methyl)piperidin-2-yl))benzoic acid, or a pharmaceutically acceptable salt thereof, which is capable of inhibiting the activation of the alternative pathway of the complement system. The complement system plays a major role in the innate and adaptive immunity system and comprises a group of proteins that are normally present in an inactive state. These proteins are organized in three activation pathways: the classical, the lectin, and the alternative pathways (Holers, In Clinical Immunology: Principles and practice, ed. R. R. Rich, Mosby Press; 1996, 363-391). Molecules from microorganisms, antibodies or cellular components can activate these pathways resulting in the formation of protease complexes known as the C3-convertase and the C5-convertase. The classical pathway is a calcium/magnesium-dependent cascade, which is normally activated by the formation of antigen-antibody complexes. It can also be activated in an antibody-independent manner by the binding of C-reactive protein complexed to ligand and by many pathogens including gram-negative bacteria. The alternative pathway is a magnesium-dependent cascade, which is activated by deposition and activation of C3 on certain susceptible surfaces (e.g. cell wall polysaccharides of yeast and bacteria, and certain biopolymer materials). The alternative pathway (AP) utilizes C3 fragments (C3b) to opsonize the pathogens hence targeting them for phagocytosis without the need for antibodies. Hyperactivity of the complement system, and in particular in its AP, plays a role in a large number of complement-driven diseases, such as C3 glomerulopathy (C3G), paroxysmal nocturnal hemoglobinuria (PNH) and IgA nephropathy (IgAN). Phenylpiperidinyl indole derivatives, such as compound of formula (I), or a pharmaceutically acceptable salt thereof, play a role in the inhibition of complement factor B, a known critical enzyme for activation of the alternative complement pathway (Lesavre et al *J. Exp. Med.* 1978, 148, 1498-1510; Volanakis et al *New Eng. J. Med.* 1985, 312, 395-401), which may also be a suitable target for the inhibition of the amplification of the complement pathways. The phenylpiperidinyl indole derivatives, such as compound of formula (I), or a pharmaceutically acceptable salt thereof, and a method for preparing such derivatives, are described in WO2015/009616. In particular, compound of formula (I) is described in example 26, of WO2015/009616. One of the drawbacks of the synthesis was the use of hazardous chemicals (such as sodium hydride, or dimethylacetamide, which represent safety concerns on a larger scale) and the poor enantio- and diastereo-selectivity of the steps, leading to unwanted stereoisomers.

Thus, there is a need to provide an alternative reaction route in a process for producing compound of formula (I), or a pharmaceutically acceptable salt thereof, generating less by-products, and easier to handle on a large scale.

SUMMARY OF THE INVENTION

Chemical processes are usually carried out on a small scale in a research/early development phase, and the scale successively increases in late phase development to finally reach the full size production scale. Upon scaling up a process, topics related to process safety are becoming more and more important, such as health hazards while handling large amount of hazardous and/or toxic chemicals, or environmental hazards.

Surprisingly, it was found that the compound of formula (I), or a pharmaceutically acceptable salt thereof, also referred to as 4-((2S,4S)-(4-ethoxy-1-((5-methoxy-7-methyl-1H-indol-4-yl)methyl)piperidin-2-yl))benzoic acid, or a pharmaceutically acceptable salt thereof, and the intermediates thereof, can be prepared with a shorter, cost efficient and safer method. Therefore, the present invention is directed to a new synthesis of compound of formula (I) and its intermediates, using less hazardous chemicals and/or reaction conditions, generating less by-product and providing a reproducible process that is easier to handle on a larger scale, a process that involves fewer reactions steps, thus more efficient, and generates high quality compounds.

In one embodiment, the invention provides a process for preparing a compound of formula (C15), or a salt thereof, as disclosed herein, said process comprising the step of reacting a compound of formula (II), or a salt thereof, as disclosed herein, with a compound of formula (III), or a salt thereof, as disclosed herein, in the presence of an Iridium catalyst, under hydrogen pressure, optionally in the presence of an additive, to provide the compound of formula (C15), or a salt thereof.

In another embodiment, the invention provides a process for preparing a compound of formula (S)-(C4), as disclosed herein, comprising reacting a compound of formula (C6) with an aryl-boronyl compound of formula (C7), as disclosed herein, in the presence of a catalyst, and a ligand, to obtain the compound of formula (S)-(C4).

In another embodiment, the invention provides a process for preparing a compound of formula (S)-(C5), as disclosed herein, the process comprising the steps of:
(i) preparing a compound of formula (S)-(C4), as disclosed herein, according to the process described herein; and
(ii) treating the compound of formula (S)-(C4), obtained from step (i), under reductive enzymatic conditions, as disclosed herein;
to obtain the compound of formula (S)-(C5).

In another embodiment, the invention provides a process for preparing a compound of formula (S)-(C9), as disclosed herein, the process comprising the steps of
(i) reacting the alcohol of the compound of formula (S)-(C5), as defined herein, with an oxygen protecting group $P_2$, to obtain a compound of formula (S)-(C8), as disclosed herein,
(ii) reacting the protected alcohol of the compound of formula (S)-(C8) with an ethylating reagent such as 2,4,6-trimethyl-1,3,5-trioxane;
to obtain a compound of formula (S)-(C9).

In another embodiment, the invention provides a compound of formula (C13), as disclosed herein.

In another embodiment, the invention provides a process for preparing a compound of formula (C13), as disclosed herein, the process comprising the steps of reacting a compound of formula (C12), as disclosed herein, with a Grignard reagent, in the presence of an aldehyde source, to obtain the compound of formula (C13).

In another embodiment, the invention provides a process for preparing a compound of formula (III), or a salt thereof, as disclosed herein, the process comprising reacting the compound of formula (C13), with an inorganic base, in the presence of an methylating agent, to obtain a compound of formula (III), or a salt thereof.

In another embodiment, the invention provides a process for preparing a compound of formula (III), or a salt thereof, as disclosed herein, the process comprising the steps of:
(i) preparing the compound of formula (C13), as disclosed herein; and
(ii) further reacting the compound of formula (C13), as disclosed herein;
to obtain the compound of formula (III), or a salt thereof.

In another embodiment, the invention relates to the use of a compound of formula (C13), as disclosed herein, for preparing a compound of formula (I), or a pharmaceutically acceptable salt thereof.

In another embodiment, the invention relates to a process for preparing a pharmaceutical composition, the process comprising the process, as disclosed herein, and mixing the obtained compound of formula (I), or a pharmaceutically acceptable salt thereof, with a pharmaceutically acceptable excipient.

BRIEF DESCRIPTION OF FIGURES

FIG. 1 depicts the X-ray powder diffraction pattern for the maleic salt of methyl 4-((2S,4S)-4-ethoxypiperidin-2-yl) benzoate (maleic salt of Compound of formula (II)).

DETAILED DESCRIPTION OF THE INVENTION

Increasing the amount of reactants and solvents in order to scale up a process to a full size commercial production may be associated with lower yields, or some safety issues while handling large amount of hazardous and/or toxic chemicals.

Surprisingly, it was found that modifying the process, as described in WO2015/009616, to synthesize compound of formula (I), or a pharmaceutically acceptable salt thereof, and its synthetic intermediates, in a way as disclosed herein provides a scalable method that can safely be handled on a larger scale, with reproducible yields, using less hazardous/toxic chemicals. In addition, this process provides the desired compound with high enantio- and diastereo-selectivity and produces compound of formula (I), or a pharmaceutically acceptable salt thereof, in fewer synthetic steps. A summary of the overall process is shown in Scheme 1, vide infra.

Scheme 1

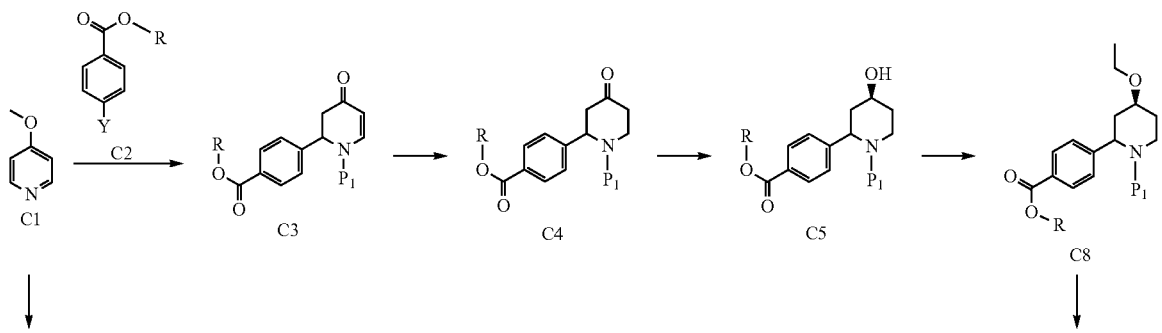

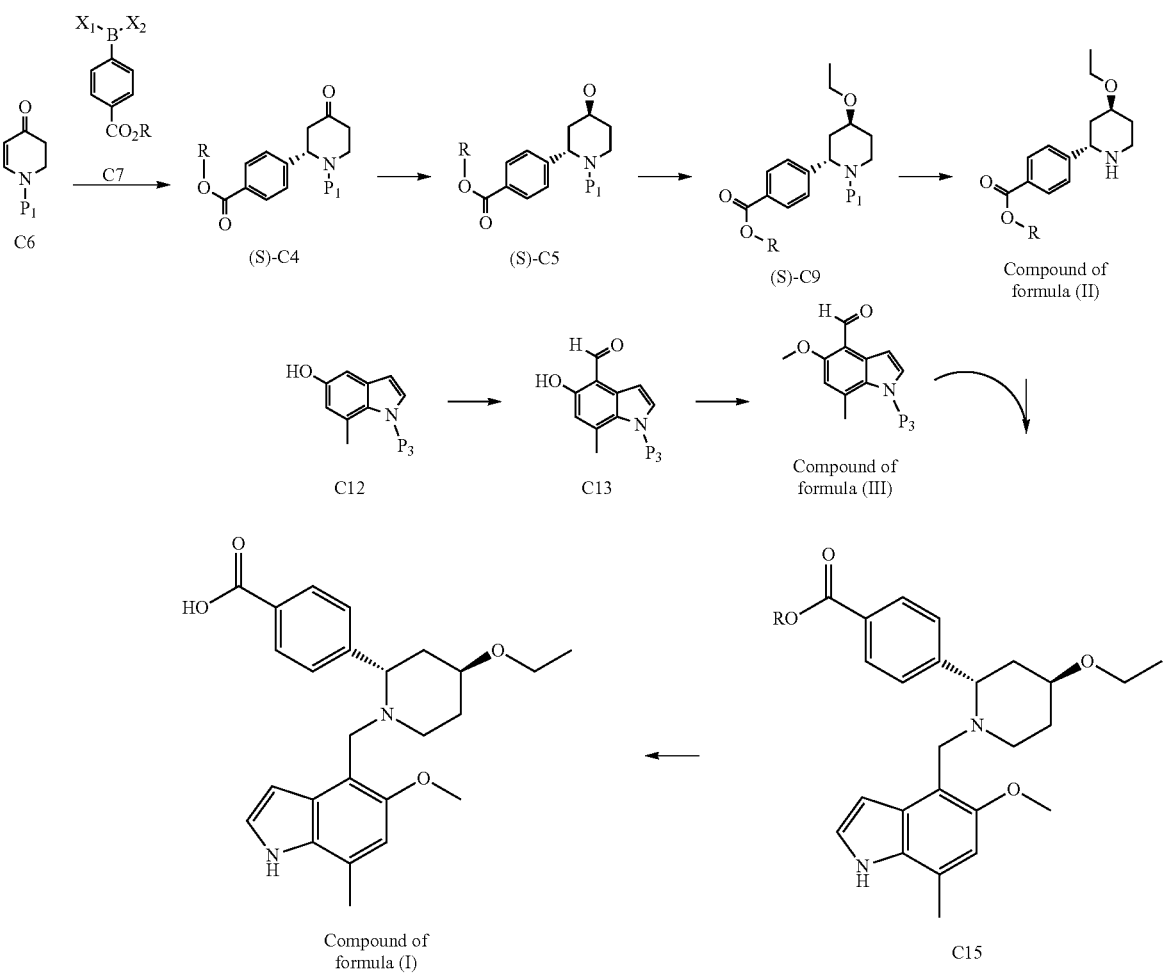

1. Asymmetric Synthesis of Compound of Formula (II):
(C1)→(C6)→(S)-(C4)→(S)-(C5)→(II).

One aspect of the present invention relates to an asymmetric process for preparing a compound of formula (II), or salt thereof, as outlined in Scheme 2 below, wherein the stereocenters in position 2 and in position 4 on the piperidine are obtained in high enantio- and diastereo-selectivity.

Scheme 2

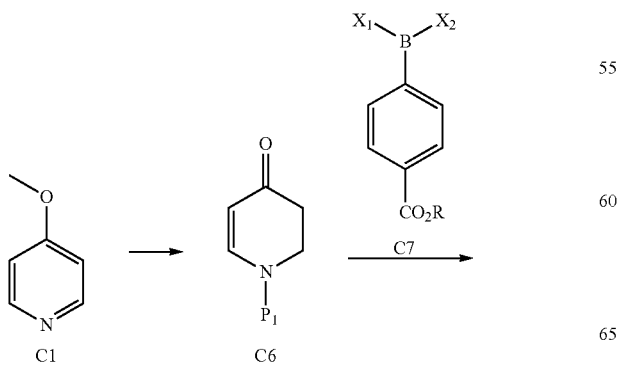

-continued

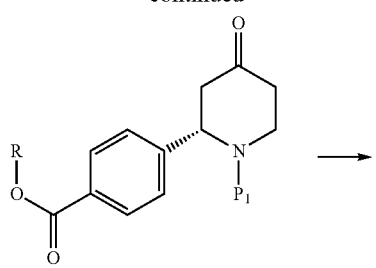

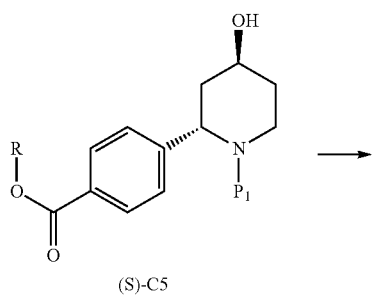

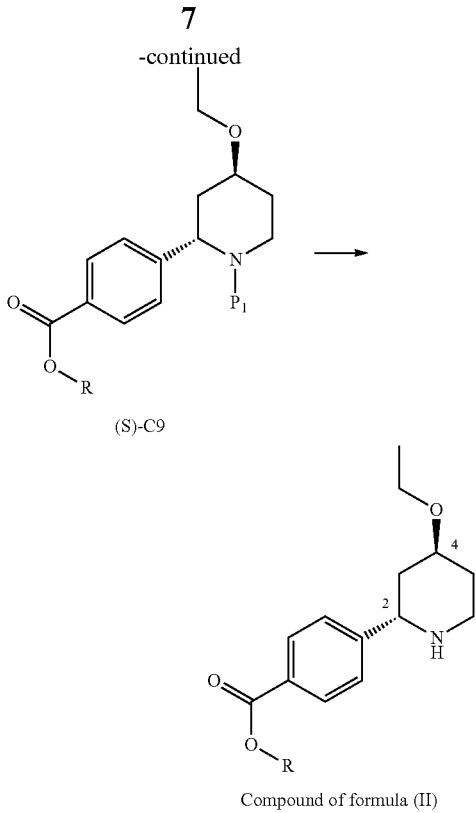

(S)-C9

Compound of formula (II)

1.1. Synthesis of Compound of Formula (S)-(C4)

In one embodiment, the present invention relates to a process for preparing a compound of formula (S)-(C4), as defined below, comprising the step of reacting a compound of formula (C6) with an aryl-boronyl compound of formula (C7), in the presence of a catalyst, and a ligand, to obtain the compound of formula (S)-(C4), as defined in Scheme 3, Scheme 3

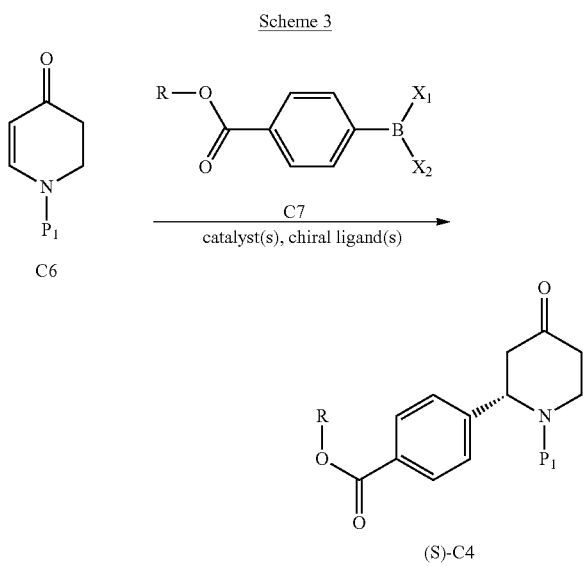

wherein
$P_1$ is a nitrogen protecting group, for example, selected from the group consisting of tert-butyloxycarbonyl (Boc), benzyl (Bz), benzyloxycarbonyl (Cbz), and allyloxycarbonyl (Alloc), preferably the nitrogen protecting group is benzyloxycarbonyl (Cbz); and R is $C_1$-$C_6$alkyl, preferably R is methyl.

The intermediate compound of formula (C6), as described in Scheme 3, can be prepared according to any literature and textbooks available to the skilled person in the art. For example, compound of formula (C6) can be prepared from a compound of formula (C1) as disclosed in Scheme 1 (e.g. following Knapp et al *J. Org. Chem.* 2005, 70(19), 7715, first experimental procedure on page 7718).

The catalyst used for the enantioselective conjugate addition between a compound of formula (C6) and an aryl-boronyl compound of formula (C7), as described in Scheme 3, can be selected, for example, from the group consisting of Rh(acac)($C_2H_4$)$_2$, Rh(nbd)$_2$BF$_4$, Rh(COD)BF$_4$, Rh(acac) (COD), [Rh(COD)Cl]$_2$, [Rh(COD)OMe]$_2$, [Rh(MeCN)$_2$(COD)]BF$_4$, [RhCl(S)-BINAP]$_2$, [Rh(OH)((S)-BINAP)]$_2$, (NHC—Pd(II)), and Pd($O_2CCF_3$)$_2$. The reaction as described in Scheme 3 is best performed in the presence of a rhodium catalyst. Preferably, the catalyst is selected from the group consisting of Rh(acac)($C_2H_4$)$_2$, Rh(nbd)$_2$BF$_4$, and Rh(COD)BF$_4$. Most preferably, the catalyst is Rh(acac)($C_2H_4$)$_2$. The catalyst can be present in an amount below 15 mol % respective to the amount of compound of formula (C6). Typically, the catalyst may be present in an amount below 5 mol %. Most preferably, the catalyst may be present in an amount from 0.01 mol % to 2 mol %.

The ligand used to perform the reaction, as depicted in Scheme 3, can be selected from the group consisting of (S)-BINAP ((S)-(2,2'-bis(diphenylphosphino)-1,1'-binaphthyl)), (S)-Tol-BINAP ((R)-(+)-2,2'-Bis(di-p-tolylphosphino)-1,1'-binaphthyl), (S)-SDP ((S)-(−)-7,7'-Bis(diphenyl phosphino)-2,2',3,3'-tetrahydro-1,1'-spirobiindene), (R)-SegPhos ((R)-(+)-5,5'-Bis(diphenyl phosphino)-4,4'-bi-1,3-benzodioxole), (R)-(+)-MeO-BIPHEP ((R)-(+)-(6,6'-Dimethoxybiphenyl-2,2'-diyl)bis(diphenylphosphine)), (S,S)-Me-Ferrocelane (1,1'-Bis[(2S,5S)-2,5-dimethylphospholano] ferrocene), chiral Josiphos ligand, (S)-(−)XylBINAP (1,1'-Binaphthalene-2,2'-diylbis[bis(3,5-dimethylphenyl)phosphine]), (S,S)-Me-DUPHOS ((+)-1,2-Bis[(2S,5S)-2,5-dimethylphospholano] benzene), (S,S)-Et-DUPHOS ((+)-1,2-Bis[(2S,5S)-2,5-diethylphospholano] benzene), (R,R)-iPr-DUPHOS (((+)-1,2-Bis[(2S,5S)-2,5-diisopropylphospholano]benzene)), and (R,R)-Ph-BPE ((+)-1,2-Bis((2R,5R)-2,5-diphenylphospholano)ethane). Preferably, the ligand is selected from the group consisting of (S)-(−)XylBINAP, (S,S)-Me-DUPHOS, (S,S)-Et-DUPHOS, (R,R)-Ph-BPE, or mixtures thereof. More preferably, the ligand is selected from the group consisting of (S)-(−)XylBINAP, (R,R)-Ph-BPE, or mixtures thereof. The ligand can be present in a range from about 0.005 mol % to about 5 mol %, respective to the amount of compound of formula (C6). Most preferably, the ligand may be present in an amount from about 0.01 mol % to about 3 mol %. Typically, the ligand is present in an amount below 2 mol %.

The reaction described in Scheme 3 can be performed in a solvent selected from, for example, 1,4-dioxane, tetrahydrofuran (THF), 2-methyl tetrahydrofuran, diethyl ether, toluene, dimethylformamide (DMF), dimethylacetamide (DMA), water, methanol, ethanol, n-propanol, 2-propanol, n-butanol, 2-butanol, tert-butanol, tert-amyl alcohol, cyclopentyl methyl ether (CPME), or mixtures thereof. The preferred solvent of the reaction is one or more solvents selected from dimethylformamide (DMF), tert-amyl alcohol, toluene, cyclopentyl methyl ether (CPME), tetrahydrofuran (THF), 2-methyl tetrahydrofuran, water, or mixtures thereof. Most preferably, the solvent is a mixture of tert-amyl alcohol and water. The ratio (volume to volume) of said mixture may be in the range from 20:1 to 1:20. Most preferably, the ratio is in the range from 15:1 to 10:1. Typically, the ratio is about 10:1, such that there is an excess of tert-amyl alcohol over water.

The substituents $X_1$ and $X_2$ on the aryl-boronyl compound of formula (C7), can be identical or different, and can be halogen, hydroxy, $C_1$-$C_4$alkoxy, hydrogen or $C_1$-$C_{12}$alkyl. The substituents $X_1$ and $X_2$ can also be bridged together in a cyclic manner, for example $X_1$, $X_2$ combined are alkylene which together with the boron and the oxygen atoms form a 5- or 6-membered ring, for example to form a diol residue. For example the boron group $B(X_1)(X_2)$ on the compound of formula (C7) is selected from the group consisting of $B(OH)_2$, —$B(OC(CH_3)_2C(CH_3)_2O)$, and 9-BBN. Preferably, $B(X_1)(X_2)$ is $B(OH)_2$. The aryl-boronyl compound of formula (C7) can be commercially available, or can be prepared from commercially available starting material according to any literature and textbooks available to the skilled person in the art.

Optionally, the reaction, as described in Scheme 3, can be performed in the presence of a base. The base can be, for example, sodium carbonate, potassium carbonate, cesium carbonate, sodium bicarbonate, potassium bicarbonate, sodium acetate, potassium acetate, trisodium phosphate, potassium phosphate, lithium hydroxide, sodium hydroxide, potassium hydroxide, cesium hydroxide, barium hydroxide, sodium methoxide, potassium methoxide, sodium ethoxide, potassium ethoxide, triethylamine, N,N-diisopropylethylamine (DIPEA), sodium tertbutoxide, potassium tertbutoxide, 1,8-diazabicyclo[5.4.0]undec-7-ene (DBU), 1,4-diazabicyclo[2.2.2]octane (DABCO), potassium fluoride or cesium fluoride.

The reaction as described in Scheme 3 is advantageously performed when the nitrogen protecting group $P_1$ is benzyloxycarbonyl (Cbz), the aryl-boronyl compound of formula (C7) is 4-(methoxycarbonyl)phenyl)boronic acid ($B(OH)_2$), the catalyst is $Rh(acac)(C_2H_4)_2$, and the ligand is (S)-(−) XylBINAP or (R,R)-Ph-BPE. Preferably, the reaction is performed at a temperature between about 25° C. to about 85° C., more preferably between about 40° C. to about 70° C. Most preferably, the reaction is performed at a temperature between about 50° C. to about 60° C. Performing the reaction under those conditions is particularly advantageous as the reaction is highly efficient, the enantioselectivity is enhanced thus by-product formation is reduced. The enantioselectivity is between 84% to more than 99% ee. Thus the present step is especially suitable for large-scale manufacture. Furthermore, it was surprisingly found that the ligands used in the catalytic arylation, as described herein, can significantly enhance the performance in both reactivity and selectivity, leading to a highly enantioselective arylation.

In another embodiment, the reaction as depicted in Scheme 3 is advantageously performed when the catalyst, as disclosed herein, and the ligand, as disclosed herein, are mixed together to form a new active reagent prior to be introduced into the reaction mixture. In one embodiment, the new active reagent is a catalyst-ligand complex. The catalyst-ligand complex can be, for example, but not limited to, (R,R)-Ph-BPE-Rh(Acac) or (S)-XylBINAP-Rh(Acac). It was surprisingly found that mixing the catalyst and the ligand to form a complex is advantageous when the reaction is performed in the presence of an air sensitive catalyst. The new catalyst-ligand complex has the advantage to be more active and less air sensitive. Thus, lower amounts of catalyst are needed to perform the reaction, as depicted in Scheme 3, in high yield.

In one embodiment, the compound of formula (I), or a pharmaceutically acceptable salt thereof, can be prepared via a process comprising the steps of preparing a compound of formula (S)-(C4) by reacting a compound of formula (C6) with an aryl-boronyl compound of formula (C7) in the presence of a catalyst and a ligand, to obtain the compound of formula (S)-(C4), as defined in Scheme 3.

1.2. Synthesis of Compound of Formula (S)-(C5)

In another embodiment, the present invention relates to a process for preparing a compound of formula (S)-(C5), as defined herein below, the process comprising the steps of:
(i) preparing a compound of formula (S)-(C4) according to the process of Section 1.1; and
(ii) treating the compound of formula (S)-(C4), obtained from step (i), under reductive enzymatic conditions;
to obtain the compound of formula (S)-(C5), as defined in Scheme 4.

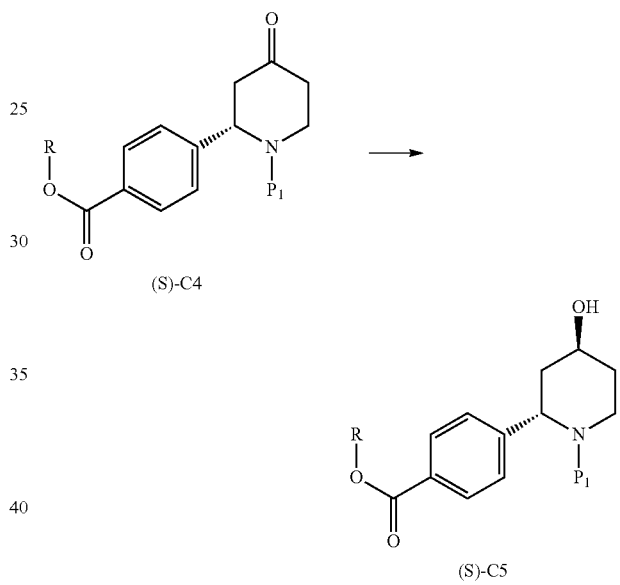

Scheme 4

(S)-C4

(S)-C5 wherein R is $C_1$-$C_6$alkyl, preferably R is methyl; and
wherein $P_1$ is a nitrogen protecting group, as defined above in Section 1.1.

The reductive enzymatic conditions, as disclosed herein, comprise treating a compound of formula (S)-(C4) with an enzyme, a co-factor, in an aqueous buffer solution, optionally in the presence of a surfactant, to provide a compound of formula (S)-(C5), as defined herein. In one embodiment, the reductive enzymatic conditions are enzymatic catalyzed conditions.

The enzyme used to perform the reaction outlined in Scheme 4, is any enzyme suitable to perform the above transformation. Suitable enzymes for use in the present reaction mixture include, for example, ketoreductases (KRED), alcohol dehydrogenases, glucose dehydrogenase (GDH), or mixtures thereof. Preferably, the enzyme is a ketoreductase (KRED). Optionally, the reaction can comprise a second enzyme, so-called co-enzyme, for example, glucose dehydrogenase (GDH). Suitable ketroreductase (KRED) used in the present invention were purchased from Codexis Inc. (Codex® KRED screening kit), and are described e.g. in WO 2005/017135, WO 2008/103248, WO2009/029554, WO2009/036404, WO2016/130412, and WO2018/013710. The KRED-EW124 enzyme was purchased from Enzyme Works Inc. China. Suitable ketoreductase can be selected from, for example, but not limited to, the group consisting of KRED-EW124, KRED-P3-G09, KRED-P1-B02, KRED-P1-C01, KRED-P2-B02, KRED-P2-C02, KRED-P3-B03, KRED-P2-D03, KRED-P2-D11, KRED-P2-D12, KRED-P2-H07, KRED-P3-H12, KRED-101, KRED-119, or mixtures thereof. Preferably, the ketroreductase (KRED) is selected from KRED-EW124, KRED-P3-G09, or mixtures thereof.

The enzyme is present in the reaction mixture in a concentration suitable to perform the reaction as outlined in Scheme 4, for example in an amount of about 0.01% to about 100% relative to the amount of compound of formula (S)-(C4). In particular, the enzyme may be present in an amount of about 0.1% to about 75%, about 0.5% to about 50%, about 1% to about 40%, about 2% to about 30%, about 4% to about 25% or about 5% to about 20%, relative to the amount of the compound of formula (S)-(C4).

The reaction as outlined in Scheme 4, further comprises a co-factor. The presence and type of the co-factor depends on the enzymatic reaction, which is to be performed. The co-factor can be selected, for example, from the group consisting of nicotinamide adenine dinucleotide (NAD), nicotinamide adenine dinucleotide phosphate (NADP), flavin adenine dinucleotide (FAD), pyridoxal monophosphate, or mixtures thereof. The co-factor may be used to provide protons, or electrons for the enzymatic reaction. In another aspect, the co-factor may be present in the reaction mixture in an ionic form, such as, for example, NAD+, NADP+. In another aspect, the co-factor may be present in the reaction mixture in a protonated form, such as, for example, NAD-H, NADP-H, or NADP-Na. In another aspect, the reaction is an enzymatic catalyzed reaction. For example, the reaction mixture may comprise a further enzyme, so called co-enzyme, which regenerates the co-factor. For example, if NAD, NADP or FAD is used as co-factor, the aqueous reaction mixture may further comprise a dehydrogenase such as an alcohol dehydrogenase, or a glucose dehydrogenase, and a respective substrate such as an alcohol or glucose. The co-factor may be present in the aqueous reaction mixture in stoichiometric amounts. For example, the molar amount may be at least as high as the molar amount of the compound of formula (S)-(C4). In another aspect, the amount of co-factor is lower than the amount of the compound of formula (S)-(C4), in particular in the range from about 0.01% to about 20%, about 0.05% to about 15%, about 0.1% to about 10%, about 0.25% to about 7.5%, or about 0.5% to about 5% relative to the amount of the compound of formula (S)-(C4).

The reaction as outlined in Scheme 4, is performed in an aqueous buffer solution. The buffer solution should be suitable to keep the pH of the reaction mixture at, or about, a neutral pH. The aqueous reaction mixture preferably has a pH at which the enzyme is active and stable, and which is suitable for the enzymatic reaction. In certain embodiments, the pH value is in the range from about 6.0 to about 8.0. More preferably, the pH is from about 6.5 to about 7.5, such as about 7.0. The buffer can be selected from the group consisting of 2-Amino-2-(hydroxymethyl)propane-1,3-diol (TRIS), 4-(2-hydroxyethyl)-1-piperazineethanesulfonic acid (HEPES), 3-(N-morpholino)propanesulfonic acid (MOPS), piperazine-N,N'-bis(2-ethanesulfonic acid (PIPES), borate, glycine, triethanol amine, phosphate, citrate, acetate and ammonia. More particularly, the buffer solution is a phosphate buffered saline (PBS) solution.

The reaction as described in Scheme 4 may also be performed in the presence of a surfactant. Suitable surfactant can be selected, for example, from vitamin E, tocopherol, α-tocopherol, and tocopherol polyethylene glycol succinates (TPGS). In particular, the surfactant is TPGS. Suitable tocopherol polyethylene glycol succinates (TPGS) surfactant can be selected, for example, but not limited to, from DL-α-tocopherol polyethylene glycol succinates such as TPGS-750-M, TPGS-1000, TPGS-1500, TPGS-400, TPGS-1100-M, TPGS-2000, TPGS-860-oleate, TPGS-PEG-PPG-PEG-1100, and TPGS-PPG-PEG-70-butyl; and DL-α-tocopherol polypropylene glycol succinates such as TPPG-1000 and TPPG-1000-butyl; and polyethylene glycol α-tocopherol diester of sebacic acid (PTS) such as PTS-600. Preferably, the surfactant is selected from the group consisting of TPGS-750-M, TPGS-1000 and PTS. Most preferably, the surfactant is TPGS-750-M.

The reaction as described in Scheme 4 is advantageously performed when the enzyme is a ketoreductase (KRED), the co-factor is nicotinamide adenine dinucleotide phosphate (NADP), preferably NADP-Na, in an aqueous buffer solution comprising a surfactant. In particular, the reaction is performed particularly well when the buffer solution is a mixture of a phosphate buffered saline (PBS) solution comprising a TPGS-750-M surfactant. Preferably, the reaction is performed at a temperature between about 30° C. to about 90° C., more preferably between about 40° C. to about 70° C. Most preferably, the reaction is performed at a temperature of about 50° C. Performing the reaction under those conditions is particularly advantageous as the reaction provides an environmentally friendly and scalable method of reducing a ketone into an alcohol, as the reaction is performed in aqueous media. Furthermore, the reaction is diastereoselective providing the desired alcohol in high yield, thus avoiding mixtures of diastereoisomers as by-products.

In one embodiment, the compound of formula (I), or a pharmaceutically acceptable salt thereof, can be prepared via the process comprising the steps of reacting a compound of formula (S)-(C4) using an enzyme, a co-factor and optionally a co-enzyme, in an aqueous buffer solution, optionally in the presence of a surfactant, to provide a compound of formula (S)-(C5), and reacting further the compound of formula (S)-(C5) to obtain the compound of formula (I), or a pharmaceutically acceptable salt thereof.

In another embodiment, the invention provides a useful intermediate for the synthesis of a compound of formula (II), or a salt thereof, a compound of formula (S)-(C5):

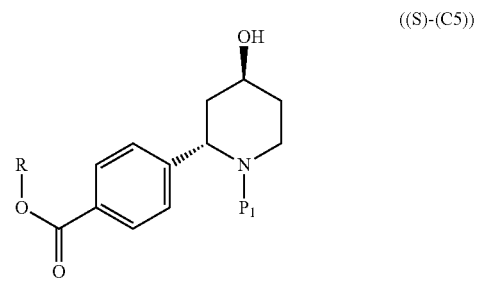

((S)-(C5))

wherein R is $C_1$-$C_6$alkyl, preferably R is methyl; and $P_1$ is a nitrogen protecting group, as defined above in Section 1.1.

In another embodiment, the invention provides the use of a compound of formula (S)-(C5) for preparing a compound of formula (II), or a salt thereof.

In another embodiment, the invention provides the use of a compound of formula (S)-(C5) for preparing a compound of formula (I), or a pharmaceutically acceptable salt thereof.

1.3. Synthesis of Compound of Formula (II), or a Salt Thereof

In another embodiment, the invention provides a process for preparing a compound of formula (S)-(C9), as outlined in Scheme 5, the process comprising the steps of:

(i) reacting the alcohol of the compound of formula (S)-(C5), with an oxygen protecting group $P_2$, to obtain a compound of formula (S)-(C8), (ii) reacting the protected alcohol of the compound of formula (S)-(C8) with an ethylating reagent, such as 2,4,6-trimethyl-1,3,5-trioxane;

to obtain a compound of formula (S)-(C9).

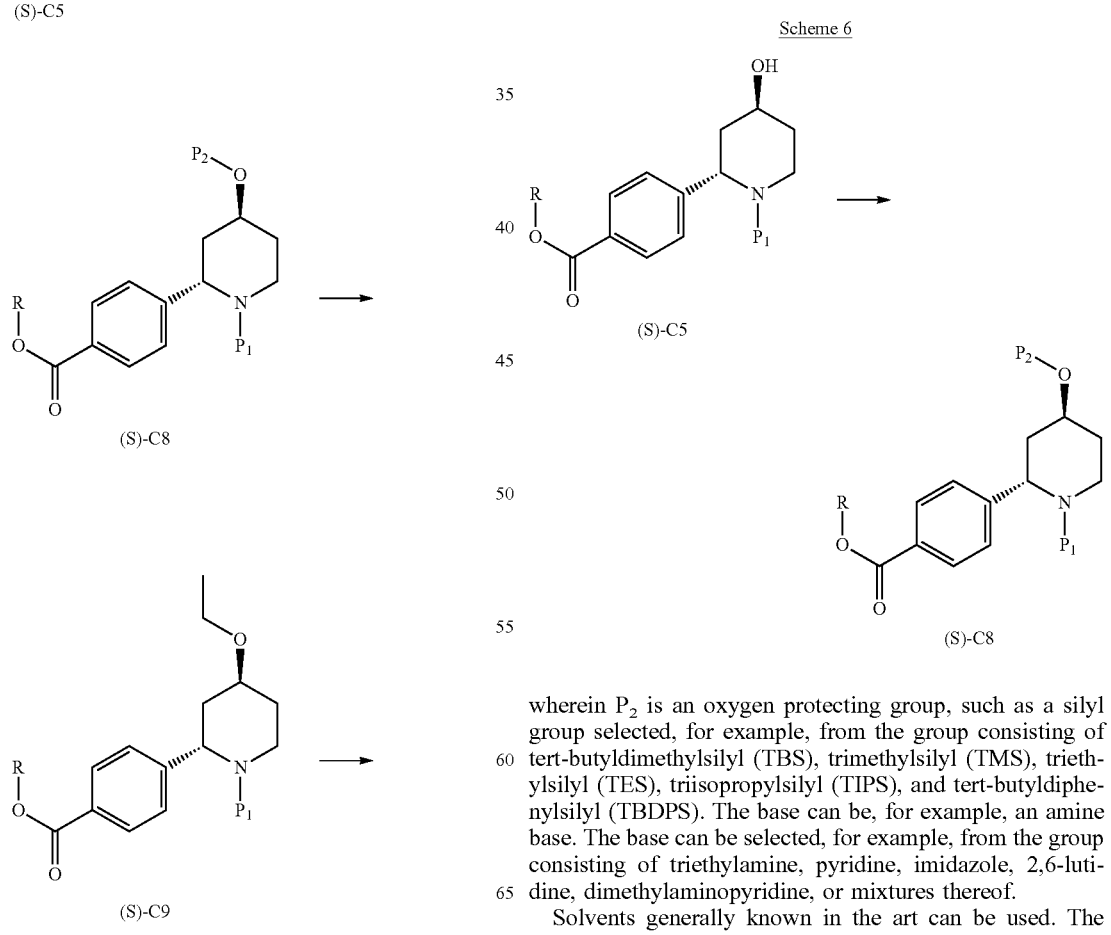

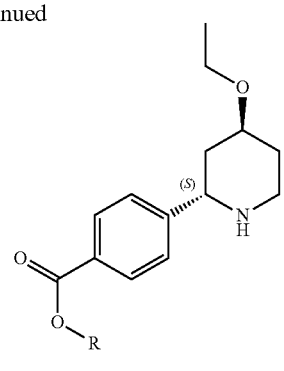

Compound of formula (II)

wherein R is $C_1$-$C_6$alkyl, preferably methyl;

wherein $P_1$ is a nitrogen protecting group as defined above in Section 1.1; and wherein $P_2$ is an oxygen protecting group. Preferably, the oxygen protecting group $P_2$ is a silyl group selected, for example, from the group consisting of tert-butyldimethylsilyl (TBS), trimethylsilyl (TMS), triethylsilyl (TES), triisopropylsilyl (TIPS), and ted-butyldiphenylsilyl (TBDPS). Most preferably $P_2$ is tert-butyldimethylsilyl (TBS).

The alcohol group of compound of formula (S)-(C5) is protected with an oxygen protecting group $P_2$ in the presence of a base, in a solvent, to obtain a first intermediate of formula (S)-(C8), as outlined in Scheme 6, wherein $P_2$ is an oxygen protecting group, such as a silyl group selected, for example, from the group consisting of tert-butyldimethylsilyl (TBS), trimethylsilyl (TMS), triethylsilyl (TES), triisopropylsilyl (TIPS), and tert-butyldiphenylsilyl (TBDPS). The base can be, for example, an amine base. The base can be selected, for example, from the group consisting of triethylamine, pyridine, imidazole, 2,6-lutidine, dimethylaminopyridine, or mixtures thereof.

Solvents generally known in the art can be used. The solvent is selected, for example, from the group consisting of isopropanol, ethanol, dimethylformamide, acetonitrile, tetrahydrofuran, 2-methyl-tetrahydrofuran, dichloromethane (DCM), dichloroethane (DCE), toluene, heptane, or mixtures thereof.

In another embodiment, the invention provides a useful intermediate for the synthesis of a compound of formula (II), or a salt thereof, a compound of formula (S)-(C8),

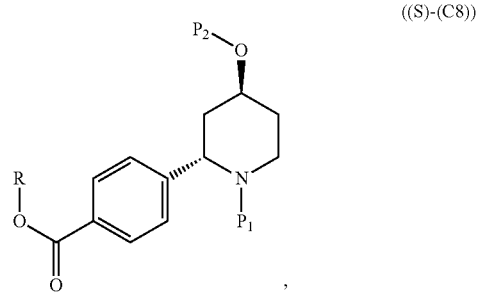

((S)-(C8))

wherein R is $C_1$-$C_6$alkyl, preferably methyl;

wherein $P_1$ is a nitrogen protecting group as defined above in Section 1.1; and wherein $P_2$ is an oxygen protecting group. Preferably, the oxygen protecting group $P_2$ is a silyl group selected, for example, from the group consisting of tert-butyldimethylsilyl (TBS), trimethylsilyl (TMS), triethylsilyl (TES), triisopropylsilyl (TIPS), and ted-butyldiphenylsilyl (TBDPS). Most preferably $P_2$ is tert-butyldimethylsilyl (TBS).

In another embodiment, the present invention provides for the use of a compound of formula (S)-(C8), for preparing a compound of formula (II), or a salt thereof.

In another embodiment, the present invention provides for the use of a compound of formula (S)-(C8), for preparing a compound of formula (I), or a pharmaceutically acceptable salt thereof.

In a next step, the oxygen protecting group $P_2$ on compound of formula (S)-(C8) is then cleaved. The resulting alcohol is reacted with an ethylating reagent, in situ, to obtain an intermediate of formula (S)-(C9), as outlined in Scheme 7, vide infra.

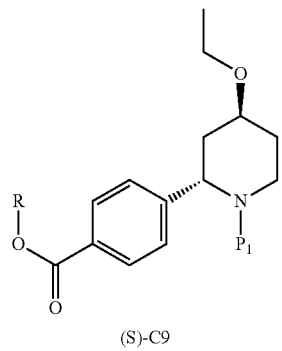

(S)-C9

Usually, any ethylating reagent known in the art is suitable. Examples of suitable ethylating reagents are ethyl iodide, ethyl bromide, ethyl chloride, ethyl fluoride, diethylsulphate, ethyl triflate (EtOTf), 4-ethylsulfonyltoluene, 2,4,6-trimethyl-1,3,5-trioxane, and mixtures thereof. Preferably the ethylating reagent is 2,4,6-trimethyl-1,3,5-trioxane.

The removal of the oxygen protecting group $P_2$ and alkylation of the free alcohol in situ can be carried out with $Et_3SiH$, an ethylating reagent, in the presence of a solvent and a Lewis acid. The Lewis acid can be selected, for example, from TESOTf, TMSBr, $BiBr_3$, TMSOTf, TBSOTf, or mixtures thereof. The reaction consisting of removing the oxygen protecting group $P_2$ can take place in a solvent that facilitates the removal of the oxygen protecting group and the alkylation. As an example, the solvent can be selected from the group consisting of dichloromethane, ethyl acetate, 1,4-dioxane, diethyl ether, tetrahydrofuran, methanol and acetonitrile. The reaction mixture is performed at a temperature between about 0° C. to about 10° C. Preferably, between about 3° C. to about 7° C. Most preferably, between about 4° C. to about 5° C.

In another embodiment, the invention relates to a process further comprising the step of reacting the compound of formula (S)-(C9) to remove the nitrogen protecting group $P_1$, to obtain the compound of formula (II), or a salt thereof, as outlined in Scheme 8 below, Scheme 7

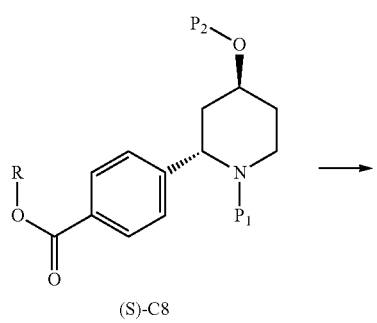

(S)-C8

Scheme 8

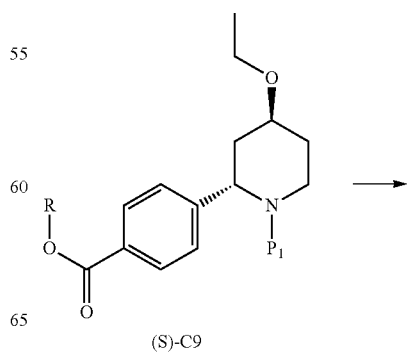

(S)-C9

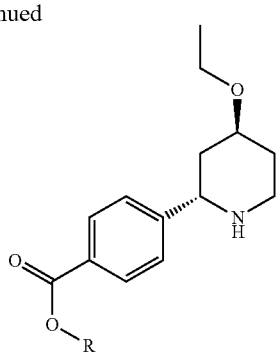

Compound of formula (II)

wherein R is $C_1$-$C_6$alkyl, preferably methyl; and
wherein $P_1$ is a nitrogen protecting group as defined above in Section 1.1.

The removal of the nitrogen protecting group $P_1$ can be carried out under standard reaction conditions known in the art. Unless otherwise specified, the nitrogen protecting group can be removed in the absence or, customarily, in the presence of acids or bases, preferably acids or bases that cause removal of the nitrogen protecting group but at the same time do not cause chemical degradation of the compounds. Preferably, the nitrogen protecting group is removed with an acid. For example, the deprotection reaction when $P_1$ is tert-butyloxycarbonyl (Boc) is best performed in acidic conditions. Particularly suitable acids for the removal of the nitrogen protecting group $P_1$ are HF.pyridine, HF.triethylamine ammonium fluoride, hexafluoroisopropanol, acetic acid, trifluoroacetic acid, hydrochloric acid, sulfuric acid, or a combination thereof. The nitrogen protecting group $P_1$ can be removed in catalytic conditions in the presence of a source of hydrogen. For example, the deprotection reaction when $P_1$ is benzyl (Bz), benzyloxycarbonyl (Cbz), or allyloxycarbonyl (Alloc), is best performed in catalytic conditions in the presence of a source of hydrogen. Particularly suitable catalyst for the removal of the nitrogen protecting group $P_1$ can be, for example, palladium on carbon (Pd/C), or palladium(II) acetate (Pd(OAc)$_2$). The reaction consisting of removing the nitrogen protecting group can take place in a solvent that facilitates the removal of the protecting group, and it is any solvent that the skilled person would select from a general textbook. As an example, the nitrogen protecting group can be removed in a solvent selected from the group consisting of dichloromethane, ethyl acetate, 1,4-dioxane, diethyl ether, tetrahydrofuran, methanol, ethanol, isopropanol and acetonitrile. For example, the deprotection reaction for the tert-butyloxycarbonyl (Boc) nitrogen protecting group is performed best with trifluoroacetic acid in dichloromethane, optionally at ambient temperature. For example, the deprotection reaction for the benzyloxycarbonyl (Cbz) nitrogen protecting group is best performed with palladium on carbon (Pd/C), under hydrogen, in isopropanol, at room temperature.

The reactions as described in Scheme 5 are advantageously performed when the alcohol on compound of formula (S)-(C5) is protected with an oxygen protecting group $P_2$ which is tert-butyldimethylsilyl (TBS), in the presence of imidazole as a base, in a mixture of acetonitrile and isopropanol, to obtain a first intermediate of formula (S)-(C8). Then the cleavage and replacement of the oxygen protecting group $P_2$ on compound of formula (S)-(C8) by an ethyl group, to obtain an intermediate of formula (S)-(C9) is best performed in the presence of TESOTf, Et$_3$SiH, 2,4,6-trimethyl-1,3,5-trioxane in acetonitrile, at a temperature between 4° C. to 5° C. Then the nitrogen protecting group $P_1$ on compound of formula (S)-(C9) is cleaved under catalytic conditions in the presence of palladium on carbon (Pd/C), hydrogen, in isopropanol, at room temperature, to obtain a compound of formula (II), or a salt thereof. Performing the protection of the alcohol group of compound of formula (S)-(C5) in two steps (first protection with $P_2$, second removal of $P_2$ and addition of an ethyl group) under those conditions is particularly advantageous as it provides reactions that are scalable avoiding any hazardous chemicals, such as sodium hydride used in WO2015/009616, without impacting the yield of the transformation. Thus, the process produces safely the compound of formula (II), or a salt thereof. In one embodiment, the compound of formula (II) is a maleic salt.

In another embodiment, the oxygen protecting group removal and the alkylation are performed sequentially, in one pot.

In one embodiment, the process comprises the steps of:

protecting the alcohol of the compound of formula (S)-(C5) with an oxygen protecting group $P_2$, to obtain a compound of formula (S)-(C8), alkylating the protected alcohol of compound of formula (S)-(C8) with an ethyl group, to obtain a compound of formula (S)-(C9), removing the nitrogen protecting group $P_1$, to obtain a compound of formula (II), or a salt thereof, and reacting further compound of formula (II), or a salt thereof, to obtain the compound of formula (I), or a pharmaceutically acceptable salt thereof.

2. Racemic Synthesis of a Compound of Formula (II): (C1)→(C3)→(C4)→(C5)→(II).

In another embodiment, the compound of formula (II), or salt thereof, can be prepared using the process as outlined in Scheme 9 below.

Scheme 9

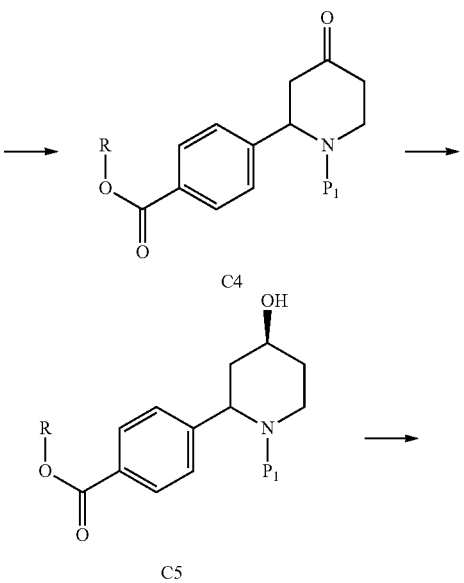

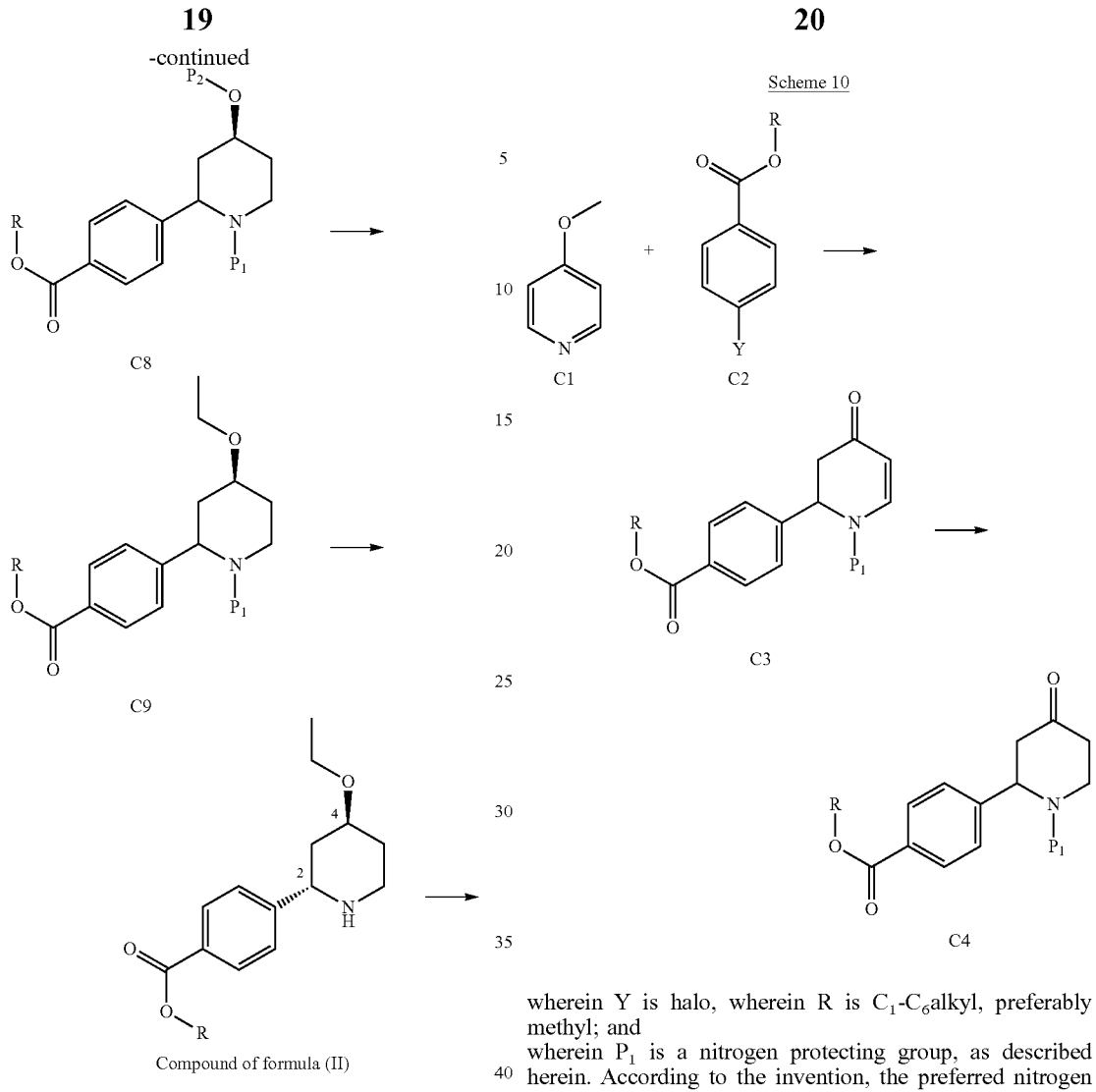

wherein R is $C_1$-$C_6$alkyl preferably methyl;

wherein $P_1$ is a nitrogen protecting group selected from the group consisting of tert-butyloxycarbonyl (Boc), benzyl (Bz), benzyloxycarbonyl (Cbz), and allyloxycarbonyl (Alloc), preferably the nitrogen protecting group is benzyloxycarbonyl (Cbz).

wherein $P_2$ is an oxygen protecting group selected for example, but not limited to, from the group consisting of tert-butyldimethylsilyl (TBS), trimethylsilyl (TMS), triethylsilyl (TES), triisopropylsilyl (TIPS), and tert-butyldiphenylsilyl (TBDPS). Most preferably, $P_2$ is tert-butyldimethylsilyl (TBS).

2.1. Synthesis of Compound of Formula (C4)

Another embodiment, the present invention relates to a process for preparing a compound of formula (C4) comprising the steps of:

reacting a compound of formula (C1), with a compound of formula (C2), in a solvent, in the presence of a ligand, a Grignard reagent, and a protecting group precursor, to form a compound of formula (C3); and further reducing the double bond of compound of formula (C3) to form the compound of formula (C4), as outlined in Scheme 10, wherein Y is halo, wherein R is $C_1$-$C_6$alkyl, preferably methyl; and wherein $P_1$ is a nitrogen protecting group, as described herein. According to the invention, the preferred nitrogen protecting group $P_1$ is selected as described above in Section 2.

The protecting group precursor used to perform the coupling reaction between a compound of formula (C1) and a compound of formula (C2), as outlined in Scheme 10, is selected depending on the nitrogen protecting group $P_1$ used to perform the transformation. For example, when $P_1$ is benzyloxycarbonyl (Cbz) the precursor is benzyl chloroformate (Cbz-Cl), when $P_1$ is benzyl (Bz) the precursor is benzoyl chloride (Bz-Cl), when $P_1$ is allyloxycarbonyl (Alloc) the precursor is allyl chloroformate (Alloc-Cl), or when $P_1$ is tert-butyloxycarbonyl (Boc) the precursor is di-tert-butyl dicarbonate ($Boc_2O$).

The ligand used to perform the reaction, as depicted in Scheme 10, can be selected from, for example, but not limited to, the group consisting of N,N,N',N',N''-pentamethyldiethylenetriamine, N,N,N',N'-tetraethylethylenediamine, bis[2-(dimethylamino)ethyl]ether, tetramethylethylene diamine, or methoxy poly(ethyleneglycol), or mixtures thereof. Preferably, the ligand is bis[2-(dimethylamino) ethyl]ether.

The Grignard reagent is, selected from, for example, the group consisting of MeMgBr, MeMgCl, EtMgBr, EtMgCl, iPrMgCl, iPrMgBr, or mixtures thereof. Most preferably, the Grignard reagent is iPrMgCl or iPrMgBr.

The first reaction described in Scheme 10, can be performed in a solvent selected, for example, from 1,4-dioxane, 4-methyl-1,3-dioxane, diglyme, tetrahydrothiophene, 2-methyltetrahydrofuran, cyclopentylmethyl ether (CPME), diethoxymethane (DEM), toluene, tetrahydrofuran (THF), diethyl ether, or mixtures thereof. Preferably, the solvent is an anhydrous solvent selected from 1,4-dioxane, tetrahydrofuran (THF), diethyl ether, or mixtures thereof. Typically, the solvent is THF.

The double bond of intermediate compound of formula (C3) can be reduced to obtain a compound of formula (C4), following the method disclosed in WO2015/009616 (page 97, Intermediate 2-12-B).

The reaction as described in Scheme 10, advantageously provides a compound of formula (C3) when performed in the presence of benzyloxycarbonyl (Cbz) chloride as protecting group precursor, iPrMgCl or iPrMgBr as Grignard reagent, and bis[2-(dimethylamino)ethyl] ether as ligand. Preferably, the reaction is performed at a temperature between 10° C. to 40° C., more preferably between 15° C. to 35° C. Typically, the reaction is best performed at a temperature from 20° C. to 30° C. Performing the reaction under those conditions is particularly advantageous as the reaction proceeds in high yield, thus making the present reaction suitable for large-scale manufacture.

In one embodiment, the process for preparing a compound of formula (I), or a pharmaceutically acceptable salt thereof, comprises the steps of preparing compound of formula (C4) by reacting a compound of formula (C1), with a compound of formula (C2), in a solvent, in the presence of a ligand, a metallic-reagent, and a protecting group precursor, to form a compound of formula (C3), and further reducing the compound of formula (C3) to form the compound of formula (C4), as outlined in Scheme 10.

2.2. Synthesis of Compound of Formula (C5)

In one embodiment, the process for preparing a compound of formula (I), or a pharmaceutically acceptable salt thereof, as defined in Scheme 1, comprises reacting a compound of formula (C4) using an enzyme, a co-factor, in an aqueous buffer solution, optionally in the presence of a surfactant, to provide a compound of formula (C5), or a salt thereof, as outlined in Scheme 11 below.

Another embodiment, the present invention relates to a process for preparing a compound of formula (C5) the process comprising the steps of:

(i) preparing a compound of formula (C4), as disclosed in the process of Section 2.1; and (ii) treating the compound of formula (C4), obtained from step (i), under reductive enzymatic conditions;

to obtain the compound of formula (C5), as outlined in Scheme 11 below,

Scheme 11

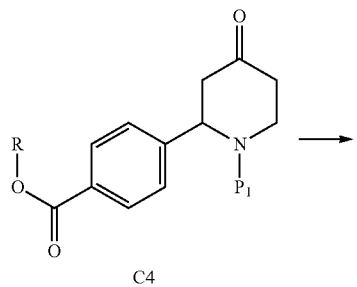

C4

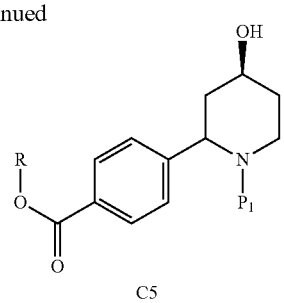

C5 wherein R is $C_1$-$C_6$alkyl, preferably methyl; and wherein $P_1$ is a nitrogen protecting group, as described above in Section 2, preferably benzyloxycarbonyl (Cbz).

The reductive enzymatic conditions, as disclosed herein, comprise treating a compound of formula (C4) with an enzyme, a co-factor, in an aqueous buffer solution, optionally in the presence of a surfactant, to provide a compound of formula (C5).

Suitable enzyme, co-factor, aqueous buffer solution, and surfactant, are the ones used to perform the reaction as described in Section 1.2. The reaction as described in Scheme 11 is advantageously performed when the enzyme is a ketoreductase (KRED), when the co-factor is nicotinamide adenine dinucleotide phosphate (NADP), in an aqueous buffer solution comprising no surfactant, and optionally comprising a second enzyme so called co-enzyme (as defined in Section 1.2). In particular, the reaction is performed particularly well when the co-enzyme is glucose dehydrogenase (GDH) and the co-factor is D-glucose. Preferably, the reaction is performed at a temperature between 30° C. to 90° C., more preferably between 40° C. to 70° C. Most preferably, the reaction is performed at a temperature of about 50° C.

Performing the reaction under those conditions is particularly advantageous as the enantioselectivity of the reduction is enhanced. In addition, the reaction is performed in mild conditions thus generating less by-products. Furthermore, the reaction provides an environmentally friendly and scalable method of reducing a ketone into an alcohol, as the reaction is performed in aqueous media.

2.3. Synthesis of Compound of Formula (II)

In one embodiment, the process comprises the following steps of:

protecting the alcohol of the compound of formula (C5), with an oxygen protecting group $P_2$, to form a compound of formula (C8), alkylating the protected alcohol on compound of formula (C8) with an ethyl group, to obtain a compound of formula (C9), removing the nitrogen protecting group $P_1$, to obtain a compound of formula (II), or salt thereof, and reacting further the compound of formula (II), or a salt thereof, to obtain the compound of formula (I), or a pharmaceutically acceptable salt thereof.

In another embodiment, the invention provides a process for preparing a compound of formula (C9), as outlined in Scheme 12 below, the process comprising the steps of:

(i) reacting the alcohol of the compound of formula (C5), with an oxygen protecting group $P_2$, to obtain a compound of formula (C8), (ii) reacting the protected alcohol of the compound of formula (C8) with an ethylating reagent;
to obtain a compound of formula (C9),

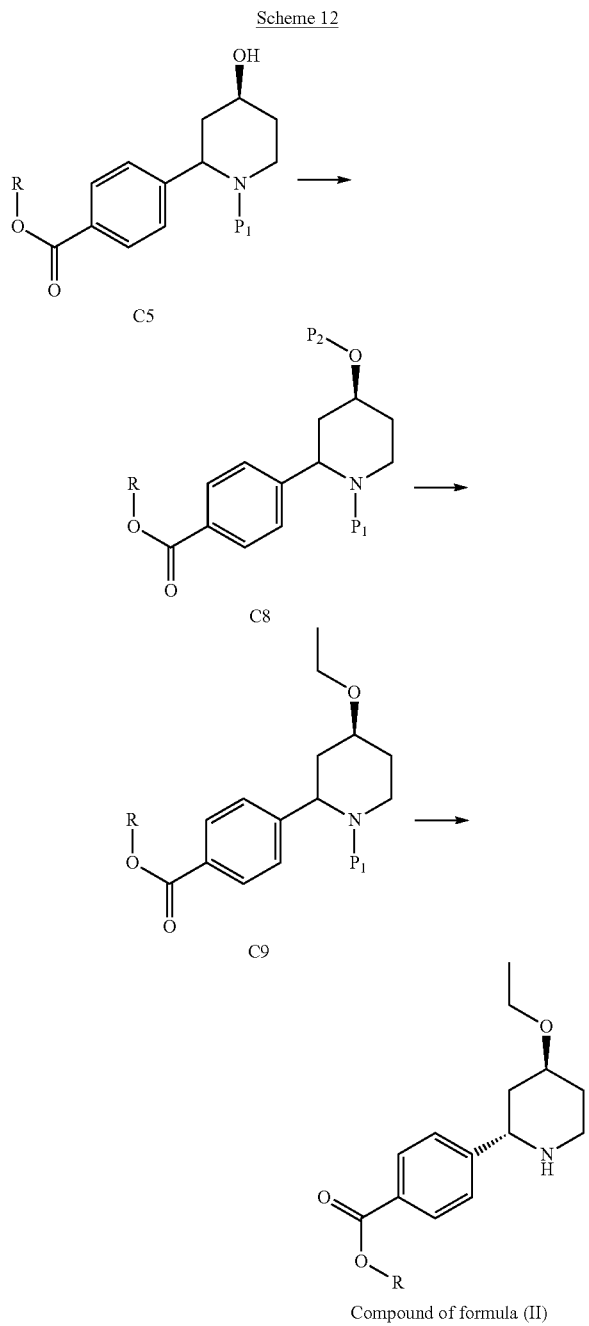

Compound of formula (II)

wherein R is $C_1$-$C_6$alkyl, preferably methyl;
wherein $P_1$ is a nitrogen protecting group. Preferably, the nitrogen protecting group $P_1$ is selected from the group consisting of tert-butyloxycarbonyl (Boc), benzyl (Bz), benzyloxycarbonyl (Cbz), and allyloxycarbonyl (Alloc). Most preferably, the nitrogen protecting group is benzyloxycarbonyl (Cbz);
wherein $P_2$ is an oxygen protecting group. Preferably, the oxygen protecting group $P_2$ is a silyl group selected, for example, but not limited to, from the group consisting of tert-butyldimethylsilyl (TBS), trimethylsilyl (TMS), triethylsilyl (TES), triisopropylsilyl (TIPS), and tert-butyldiphenylsilyl (TBDPS). Most preferably, $P_2$ is tert-butyldimethylsilyl (TBS).

The alcohol group of compound of formula (C5) is protected with an oxygen protecting group $P_2$ in the presence of a base, in a solvent, to obtain a first intermediate of formula (C8), using the same conditions as described above for the (S)-(C5) to (S)-(C8) transformation (see Section 1.3). In particular, the protection of compound of formula (C5) is performed particularly well when the oxygen protecting group $P_2$ is tert-butyldimethylsilyl (TBS), the base is imidazole, in a mixture of toluene and heptane, to obtain a first intermediate of formula (C8).

The oxygen protecting group $P_2$ on compound of formula (C8) is then cleaved and the resulting alcohol is reacted with an ethylating reagent to obtain an intermediate of formula (C9), using similar conditions as the ones described above to obtain intermediate of formula (S)-(C9) (see Section 1.3). In particular, the cleavage and replacement of the oxygen protecting group $P_2$ by an ethyl group, in situ, to obtain an intermediate of formula (C9) is advantageously performed with TESOTf, $Et_3SiH$, and 2,4,6-trimethyl-1,3,5-trioxane, in acetonitrile, at a temperature between 4° C. to 5° C. Performing the ethylation of the alcohol group under those conditions is particularly advantageous as it provides a scalable method avoiding any hazardous chemicals, such as sodium hydride (NaH) used in WO2015/009616, without impacting the yield of the transformation.

In another embodiment, the nitrogen protecting group $P_1$ on compound of formula (C9) is cleaved off, followed by a chiral resolution to obtain a compound of formula (II), or a salt thereof. The removal of the oxygen protecting group $P_1$ can be carried out under standard reaction conditions, as described above in Section 1.3 ((S)-C9 to (II)). The chiral resolution can be performed, for example, according to WO 2015/009616 (for example intermediate 2-13, on pages 96-97). The compound of formula (II) can be present in a salt form, as described above, for example, the maleic salt.

3. Synthesis of a Compound of Formula (III): (C12)→(C13)→(III).

3.1. Synthesis of a Compound of Formula (C13)

In another embodiment, the invention provides a process for preparing a compound of formula (C13), the process comprising the steps of reacting a compound of formula (C12) with a Grignard reagent or with a Lewis acid, in the presence of an aldehyde source, to obtain the compound of formula (C13), as outlined in Scheme 13.

In another embodiment, the invention provides a process for preparing a compound of formula (C13), the process comprising the steps of reacting a compound of formula (C12) with a Grignard reagent, in the presence of an aldehyde source, to obtain the compound of formula (C13), as outlined in Scheme 13, vide-infra.

Scheme 13

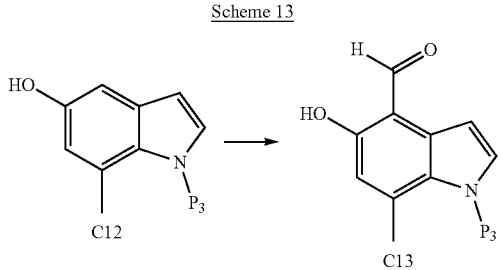

wherein P₃ is a nitrogen protecting group, selected from the group consisting of tert-butyloxycarbonyl (Boc), toluenesulfonyl (Tosyl), and trifluoromethanesulfonyl. Preferably, the nitrogen protecting group P₃ is tert-butyloxycarbonyl (Boc).

The intermediate compound of formula (C12), as described in Scheme 13 above, can be prepared according to the method disclosed in WO 2014/143638 (example 2).

The reaction as outlined in Scheme 13 can be performed in the presence of a Grignard reagent, or with a Lewis acid. The Grignard reagent used to perform the reaction, as outlined in Scheme 13, can be selected from the group consisting of MeMgBr, MeMgCl, MeMgI, EtMgBr, EtMgCl, EtMgI, iPrMgCl, iPrMgBr, iPrMgI, or mixtures thereof. Preferably, the Grignard reagent is selected from MeMgBr and MeMgCl. The Lewis acid that can be used to perform the reaction, as outlined in Scheme 13, can be selected from the group consisting of MgCl₂, MgBr₂, MgI₂ or mixtures thereof.

Optionally, the reaction, as described in Scheme 13, can be performed in the presence of a base. The base can be any suitable base that a skilled person would select based on a general textbook. The base can be for example, but not limited to, selected from, triethylamine, N,N-diisopropylethylamine (DIPEA), 1,8-diazabicyclo[5.4.0]undec-7-ene (DBU), 1,4-diazabicyclo[2.2.2] octane (DABCO), or mixtures thereof. Preferably, the base is triethylamine, DBU, or mixtures thereof.

The aldehyde source used to perform the reaction can be selected from the group consisting of formaldehyde, paraformaldehyde, urotropine, and 2,4,6-trimethyl-1,3,5-trioxane. Preferably, the aldehyde source is paraformaldehyde.

Suitable solvents that can be used for the reaction are, for example, but not limited to, 1,4-dioxane, tetrahydrofuran (THF), 2-methyl tetrahydrofuran, diethyl ether, or mixtures thereof.

The synthesis of compound of formula (C13) is advantageously performed when the Grignard reagent is MeMgBr, the aldehyde source is paraformaldehyde, and the oxygen protecting group P₂ is tert-butyloxycarbonyl. In another embodiment, the synthesis of compound of formula (C13) is also advantageously performed when the Lewis acid is MgCl₂, the aldehyde source is paraformaldehyde, and the oxygen protecting group P₂ is tert-butyloxycarbonyl. The reaction is best performed at a temperature between room temperature to reflux. The temperature may need to be higher than room temperature in order to get good yields. Particularly, when using a reactive Grignard reagent the temperature may need to be between −30° C. to reflux. The reflux temperature is preferably at about 60° C. to about 80° C., most preferably at about 65° C. to about 75° C. Performing the reaction under those conditions is particularly advantageous as the reaction provides 100% regioselectivity, thus making the present step especially suitable for a large-scale manufacture.

In one embodiment, the compound of formula (I), or a pharmaceutically acceptable salt thereof, can be prepared by a process comprising the steps of reacting a compound of formula (C12) with a Grignard reagent in the presence of an aldehyde source, to obtain a compound of formula (C13), as outlined in Scheme 13, and further reacting the compound of formula (C13) to obtain a compound of formula (I), or a salt thereof.

3.2. Compound of Formula (C13)

In another embodiment, the invention provides a useful intermediate for the synthesis of a compound of formula (III), or a salt thereof, a compound of formula (C13),

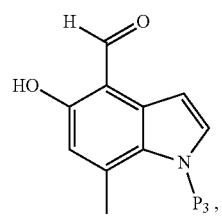

wherein P₃ is a nitrogen protecting group, as defined above in Section 3.1.

In another embodiment, the present invention provides for the use of a compound of formula (C13) for preparing a compound of formula (III), or a salt thereof.

In another embodiment, the present invention provides for the use of a compound of formula (C13) for preparing a compound of formula (I), or a pharmaceutically acceptable salt thereof.

3.3. Synthesis of Compound of Formula (III), or a Salt Thereof

In another embodiment, the present invention provides a process for preparing a compound of formula (III), or a salt thereof, the process comprising reacting the compound of formula (C13) with an inorganic base, in the presence of a methylating agent, to obtain a compound of formula (III), or a salt thereof, as outlined below in Scheme 14.

Scheme 14

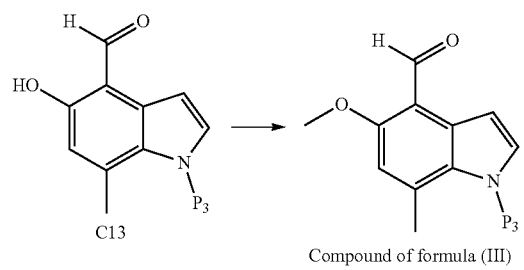

wherein P₃ a nitrogen protecting group, as defined above in Section 3.1.

The inorganic base used to perform the reaction are inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts. Preferably, the inorganic base is an alkali metal base. Examples of suitable bases are, for example, Na₂CO₃, K₂CO₃, Cs₂CO₃, or mixtures thereof. Preferably, the base is potassium carbonate (K₂CO₃).

The methylating agent that can be used to transform the alcohol into a methoxy group can be any methylating agent the skilled person would select based on general textbooks. Examples for suitable methylating agents are methyl iodide, methyl bromide, methyl chloride, dimethylsulfate, methyl triflate (MeOTf), 4-methylsulfonyltoluene, methyl benzenesulfonate and mixtures thereof. Preferably, methyl iodide, methyl benzenesulfonate, and dimethyl sulfate. Preferably, the methylating agent is dimethyl sulfate.

Suitable solvent that can be used for the reaction are, for example, dimethylformamide (DMF), dimethoxyethane (DME), tetrahydrofuran (THF), dimethyl sulfoxide (DMSO), toluene, acetonitrile or mixtures thereof. Preferably, the solvent is dimethylformamide (DMF).

The synthesis of compound of formula (III), or a salt thereof, as described in Scheme 14, is advantageously performed when the methylating agent is dimethyl sulfate, and the base is an alkali base such as potassium carbonate. In particular, the reaction performs well at a temperature of about 15° C. to about 35° C. Preferably, from about 20° C. to about 25° C.

In one embodiment, the compound of formula (I), or a pharmaceutically acceptable salt thereof, can be prepared by the process comprising the steps of preparing a compound of formula (III), or a salt thereof, by reacting a compound of formula (C13) with a base in the presence of an alkylating agent, as outlined in Scheme 14.

In another embodiment, the present invention provides a process for preparing a compound of formula (III), or a salt thereof, as disclosed herein, the process comprising the steps of:

(i) preparing the compound of formula (C13), as described in Section 3.1; and (ii) further reacting the compound of formula (C13), as described in Section 3.3;

to obtain the compound of formula (III), or a salt thereof.

4. Synthesis of a Compound of Formula (I)=(II)+(III):

4.1. Synthesis of a Compound of Formula (C15)

In one embodiment, the process for preparing a compound of formula (I), or a pharmaceutically acceptable salt thereof, comprises reacting a compound of formula (II), or a salt thereof, with a compound of formula (III), or a salt thereof, in the presence of an Iridium catalyst in a solvent, under a hydrogen pressure, optionally in the presence of an additive, to obtain a compound of formula (C15), or salt thereof, as described in Scheme 15 vide infra, In another embodiment, the present invention provides a process for preparing a compound of formula (C15), or a salt thereof, said process comprising the step of reacting a compound of formula (II), or a salt thereof, with a compound of formula (III), or a salt thereof, in the presence of an Iridium catalyst, under hydrogen pressure, optionally in the presence of an additive, to provide the compound of formula (C15), or a salt thereof, as outlined in Scheme 15 below.

Scheme 15

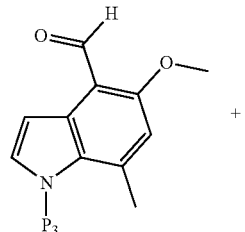

compound of
formula (III)

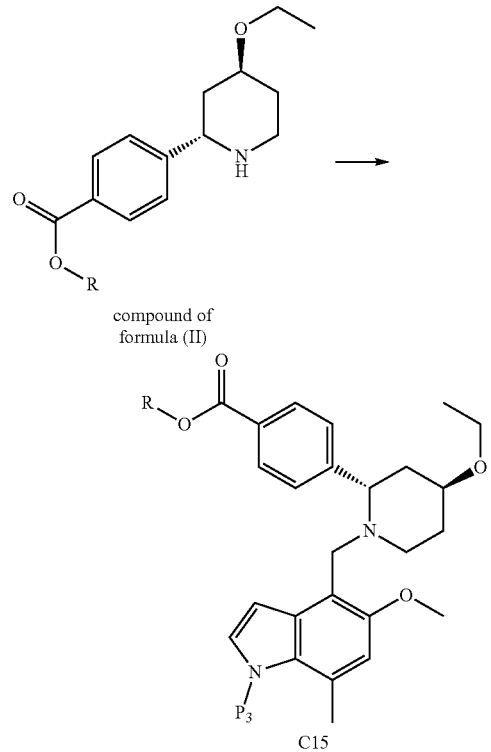

wherein $P_3$ is a nitrogen protecting group, as defined above in Section 3.1; and wherein R is a $C_1$-$C_6$alkyl, preferably R is methyl.

The catalyst used to perform the reaction can be, for example, selected from the group consisting of [Ru(Triphos)(CO)H$_2$], [Ru(S)-BINAP(p-cymene)Cl]Cl, [Ru(CO)ClH(PPh$_3$)$_3$], [Ru(R)-BINAP (benzene)Cl]Cl, Ir(CO)$_2$acac, Ir(COD)Cl, Ir(CO)$_3$, and IrCl$_3$,xH$_2$O. Preferably, the catalyst is an Iridium catalyst selected from the group consisting of Ir(CO)$_2$acac, Ir(COD)Cl, Ir(CO)$_3$, and IrCl$_3$,xH$_2$O. The catalyst can be present in a range from about 0.05 mol % to about 10.0 mol %. Preferably, the catalyst is present in a range from 0.1 mol % to about 5.0 mol %. Suitable solvents used for the reaction are, for example, methanol, ethanol, isopropanol, ethylene glycol, diethyl carbonate, DMSO, acetonitrile, tetrahydrofuran, or mixtures thereof.

The additive can be a ligand, a base, an acid, or mixtures thereof. The additive can be selected from, for example, but not limited to, the group consisting of tetrabutylammonium iodide (TBAI), ((oxydi-2,1-phenylene)bis(diphenylphosphine)) (DPEPhos), triethylamine (Et$_3$N), sodium trifluoromethanesulfonate (NaOTf), 4,5-bis(diphenylphosphino)-9,9-dimethylxanthene (Xantphos), 1,4-Diazabicyclo[2.2.2]octane (DABCO), tris(4-fluorophenyl)phosphine ((4-F—C$_6$H$_4$)$_3$P), acetic acid, N-bromosuccinimide (NBS), N-chlorosuccinimide (NCS), or mixtures thereof.

The reaction as described in Scheme 15 is performed particularly well when 0.1 mol % of Ir(CO)$_2$acac catalyst is present, in ethanol as solvent, under hydrogen pressure. In particular, the reaction performs well at a temperature in a range from about room temperature to reflux. Preferably, the temperature is in a range from about 60° C. to about 100° C. Typically, the temperature is about 80° C. The reaction is best performed in the presence of hydrogen. The pressure of hydrogen in the reaction can be in a range from about 1 bar to about 30 bar, preferably between about 2.5 bar to about 20 bar. Performing the reaction under those conditions is particularly advantageous as the reaction is highly efficient and the amount of by-product formation is reduced compared to the preparation of compound of formula (C15) described in WO 2015/009616 (Intermediate 4-3, on page 127-128).

In another embodiment, the present invention provides a process for preparing a compound of formula (C15), or a salt thereof, the process comprising the step of reacting a compound of formula (II), or a salt thereof, with a compound of formula (III), or a salt thereof, as described in Scheme 15, to prepare a compound of formula (C15), or a salt thereof, wherein the aldehyde group on the compound of formula (III), or salt thereof, is first reduced to the corresponding alcohol to obtain an intermediate compound of formula (IIIa), or a salt thereof,

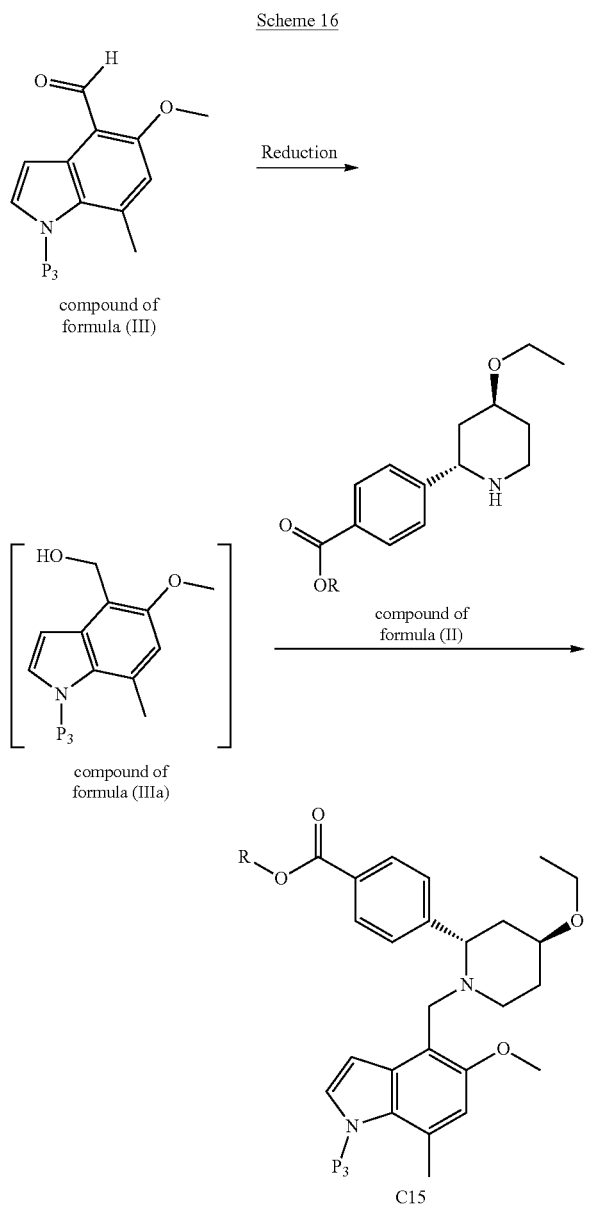

wherein $P_3$ is a nitrogen protecting group, as defined above in Section 3.1; and
wherein R is a $C_1$-$C_6$alkyl, preferably R is methyl.

The compound of formula (IIIa), or a salt thereof, is then reacted with a compound of formula (II), or salt thereof, in the presence of an Iridium catalyst in a solvent, in a hydrogen atmosphere, optionally in the presence of an additive, as described above in Section 4.1.

In another embodiment, the present invention provides for an in situ reduction of the aldehyde group on compound of formula (III), or a salt thereof, to the corresponding alcohol to obtain a compound of formula (IIIa), or a salt thereof. The compound of formula (IIIa), or a salt thereof, is then reacted with a compound of formula (II), or a salt thereof, in the presence of an Iridium catalyst in a solvent, under hydrogen pressure, optionally in the presence of an additive, as described above in Section 4.1.

4.2. Compound of Formula (I), or a Pharmaceutically Acceptable Salt Thereof

In another embodiment, the present invention provides a process as defined in Section 4.1, wherein the compound of formula (C15), or a salt thereof is further reacted under hydrolyzing conditions to obtain a compound of formula (I), or a pharmaceutically acceptable salt thereof.

The term "hydrolyzing conditions" refers to the hydrolysis of an ester group of formula —$CO_2R$, wherein R is $C_1$-$C_6$alkyl, such as methyl, to form a carboxylic acid of formula —$CO_2H$. The ester group can be hydrolyzed, for example, under basic conditions (e.g. using an alkali metal base such as NaOH, LiOH or KOH), or under acidic conditions (e.g. using mineral acids, such as HCl, $H_2SO_4$, HBr, $H_3PO_4$) to provide a carboxylic acid.

In one embodiment, the compound of formula (C15), or a salt thereof, is reacted under hydrolyzing conditions to obtain the corresponding carboxylic acid, as outlined in Scheme 1. For example, using the hydrolyzing conditions as described in WO2015/009616 (example 26, on page 174).

Certain variants, or alternative processes, to prepare a compound of formula (I), or a pharmaceutically acceptable salt thereof, are described herein below. For example, the process comprises the following steps:
(i) preparing a compound of formula (S)-(C4), as disclosed in Section 1.1,
(ii) preparing a compound of formula (S)-(C5), by reacting a compound of formula (S)-(C4); under reductive enzymatic conditions, as disclosed in Section 1.2;
(iii) preparing a compound of formula (C13), as disclosed in Section 3.2;
(iv) preparing a compound of formula (III), or a salt thereof, as disclosed in Section 3.3;
(v) reacting the compound of formula (II), or a salt thereof, with a compound of formula (III), or a salt thereof, to obtain a compound of formula (C15), or a salt thereof, as disclosed in Section 4.1; and
(vi) reacting the compound of formula (C15), or a salt thereof, under hydrolyzing conditions to obtain a compound of formula (I), or a pharmaceutically acceptable salt thereof.

In another embodiment, the present invention also provides a process for preparing a compound of formula (I), or a pharmaceutically acceptable salt thereof, as described herein below. For example, the process comprises the following steps:
(i) preparing a compound of formula (S)-(C5), by reacting a compound of formula (S)-(C4), under reductive enzymatic conditions, as disclosed in Section 1.2;
(ii) preparing a compound of formula (C13) as disclosed in Section 3.2; and (iii) reacting the compound of formula (II), or a salt thereof, with a compound of formula (III), or a salt thereof, as disclosed in Section 4.1.

In another embodiment, the present invention also provides a process for preparing a compound of formula (I), or a pharmaceutically acceptable salt thereof, the process comprising the following steps:
(i) preparing a compound of formula (C5), by reacting a compound of formula (C4), using an enzymatic catalyzed step, as disclosed in Section 2.2;
(ii) preparing a compound of formula (C13) as disclosed in Section 3.2;
(iii) preparing a compound of formula (III), or a salt thereof, as disclosed in Section 3.3;
(iv) reacting the compound of formula (II) or a salt thereof with a compound of formula (III), or a salt thereof, to obtain a compound of formula (C15), or a salt thereof, as disclosed in Section 4.1; and
(v) reacting the compound of formula (C15), or a salt thereof, under hydrolyzing conditions to obtain a compound of formula (I), or a pharmaceutically acceptable salt thereof.

In another embodiment, the present invention also provides a process for preparing a compound of formula (I), or a pharmaceutically acceptable salt thereof, the process comprising the following steps:
(i) preparing a compound of formula (C5), by reacting a compound of formula (C4), under reductive enzymatic conditions, as disclosed in Section 2.2;
(ii) preparing a compound of formula (C13) as disclosed in Section 3.2; and
(iii) reacting the compound of formula (II) or a salt thereof with a compound of formula (III), or a salt thereof, as disclosed in Section 4.1.

In yet another embodiment, the present invention relates to a process for preparing a pharmaceutical composition, the process comprising the process according to Section 4.2 and mixing the obtained compound of formula (I), or a pharmaceutically acceptable salt thereof, with a pharmaceutically acceptable excipient.

The compound of formula (I), or a pharmaceutically acceptable salt thereof, prepared as described above may optionally be further purified by recrystallization from a suitable solvent and may optionally be milled or sieved in order to obtain the final pharmaceutically active ingredient.

Once the pharmaceutically active ingredient, compound of formula (I), or a pharmaceutically acceptable salt thereof, is obtained (as described above) it can be mixed with a pharmaceutically acceptable excipient. This can be achieved by mixing, granulating, compacting and the like. This way, a pharmaceutical composition can be prepared and used for the preparation of final dosage forms, such as tablets or capsules, or any other suitable pharmaceutical composition.

Definitions

The term "catalyst" as used herein refers to a catalytic amount of a chemical agent that enhances the rate of a chemical reaction by lowering the activation energy for the chemical reaction. The catalyst can be a heterogeneous catalyst or a homogenous catalyst. The term "heterogeneous catalyst" refers to a catalyst supported on a carrier, typically although not necessarily a substrate comprised of an inorganic material, for example, a porous material such as carbon, silicon and/or aluminum oxide. The term "homogeneous catalyst" refers to a catalyst that is not supported on a carrier.

The term "one-pot" or "one-pot process" means that in a series (i.e. in a succession) of reactions, for example two or more successive reactions, each reaction product is provided for the next reaction without isolation and purification. The one-pot processes defined herein encompass not only a series (i.e. a succession) of reactions conducted in a single reaction vessel, but also a series (i.e. a succession) of reactions conducted in a plurality of reaction vessels (e.g., by transferring the reaction mixture from one vessel to other) without isolation and purification. Preferably, the one-pot process is conducted in a single reaction vessel.

The term "ligand" means any compound, achiral or chiral, that can form a complex with a transition metal. The term "chiral" refers to molecules which have the property of non-superimposability on their mirror image partner, while the term "achiral" refers to molecules which are superimposable on their mirror image partner.

The term "amount" herein refers either to the weight of the compounds or to the molar amount of the compounds.

The term "protecting group" may be present and should protect the functional groups concerned against unwanted secondary reactions, such as acylations, etherifications, esterifications, oxidations, solvolysis and similar reactions. It is a characteristic of protecting groups that they lend themselves readily, i.e. without or with very limited undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter. Preferably, if two or more protecting groups are present in one intermediate mentioned, they are chosen so that, if one of the groups needs to be removed, this can be done selectively, e.g. using two or more different protecting groups that are cleavable under different conditions, e.g. one class by mild hydrolysis, the other by hydrolysis under harder conditions, one class by hydrolysis in the presence of an acid, the other by hydrolysis in the presence of a base, or one class by reductive cleavage (e.g. by catalytic hydrogenation), the other by hydrolysis, or the like. Suitable nitrogen protecting groups are conventionally used in peptide chemistry and are described e.g. in the relevant chapters of standard reference works such as J. F. W. McOmie, "Protective Groups in Organic Chemistry", Plenum Press, London and New York 1973; T. W. Greene and P. G. M. Wuts, "Greene's Protective Groups in Organic Synthesis", Fourth Edition, Wiley, New York 2007; in "The Peptides"; Volume 3, Academic Press, London and New York 1981, and in "Methoden der organischen Chemie" (Methods of Organic Chemistry), Houben Weyl, 4th edition, Volume 15/I, Georg Thieme Verlag, Stuttgart 1974.

The term "oxygen protecting group" generally comprises any group which is capable of reversibly protecting the oxygen functionality. A hydroxyl protecting group may, for example, be selected from a group comprising (especially consisting of) a silyl protecting group, especially diarylalkyl-silyl, such as diphenyl-tert-butylsilyl, or more preferably tri-alkylsilyl, such as tert-butyldimethylsilyl or trimethylsilyl; an acyl group, e.g. alkanoyl, such as acetyl; benzoyl; alkoxycarbonyl, such as tert-butoxycarbonyl (Boc), or arylalkoxycarbonyl, such as benzyloxycarbonyl; tetrahydropyranyl; unsubstituted or substituted arylalkyl, such as benzyl or p-methoxybenzyl, and methoxymethyl. Exemplary hydroxyl protecting groups are acetyl, propionyl, butynyl, pivaloyl, 2-chloroacetyl, benzoyl; carbonate derivatives such as phenoxycarbonyl, t-butoxycarbonyl ethoxycarbonyl, vinyloxycarbonyl, 2,2,2-trichloroethoxycarbonyl and benzyloxycarbonyl; alkyl ether forming groups such as methyl, methoxymethyl, methylthiomethyl, benzyloxymethyl, t-butoxymethyl, 2-methoxyethoxymethyl, 2,2,2-trichloroethoxymethyl, 2-(trimethylsilyl)ethoxymethyl, tetrahydropyranyl, tetrahydrofuranyl, t-butyl, triphenylmethyl, benzyl, diphenylmethyl, allyl; silyl ether forming groups such as trialkylsilyl, trimethylsilyl, triethylsilyl, t-butyldimethylsilyl, t-butyldiphenylsilyl, isopropyldialkylsilyl, alkyldiisopropylsilyl, triisopropylsilyl, t-butyldialkyl-silyl; and carbamates such as N-phenylcarbamate or N-imidazoylcarbamate. In particular, a hydroxyl protecting group is a silyl group according to the formula SiR7R8R9, wherein R7, R8 and R9 are, independently of each other, alkyl or aryl. Examples for R7, R8 and R9 are methyl, ethyl, isopropyl, t-butyl and phenyl. In particular, R7, R8 and R9 are ethyl or methyl.

The term "nitrogen protecting group" generally comprise: $C_1$-$C_6$-alkyl, preferably $C_1$-$C_4$-alkyl, more preferably $C_1$-$C_2$-alkyl, (e.g. acetyl, allyl, tertbutyl) most preferably $C_1$-alkyl which is mono-, di- or tri-substituted by trialkylsilyl-$C_1$-$C_7$-alkoxy (eg. trimethylsilyethoxy), aryl, preferably phenyl, or an heterocyclic group (e.g., benzyl, cumyl, benzhydryl, pyrrolidinyl, trityl, pyrrolidinylmethyl, 1-methyl-1,1-dimethylbenzyl, (phenyl)methylbenzene) wherein the aryl ring or the heterocyclic group is unsubstituted or substituted by one or more, e.g. two or three, residues, e.g. selected from the group consisting of $C_1$-$C_7$-alkyl, hydroxy, $C_1$-$C_7$-alkoxy, $C_2$-$C_8$-alkanoyl-oxy, halogen, nitro, cyano, and $CF_3$; aryl-$C_1$-$C_2$-alkoxycarbonyl (preferably phenyl-$C_1$-$C_2$-alkoxycarbonyl (eg. benzyloxycarbonyl (Cbz), benzyloxymethyl (BOM), pivaloyloxymethyl (POM)); alkenyloxycarbonyl; $C_1$-$C_6$alkylcarbonyl (eg. acetyl or pivaloyl); $C_6$-$C_{10}$-arylcarbonyl; $C_1$-$C_6$-alkoxycarbonyl (eg. tertbutoxycarbonyl (Boc), methylcarbonyl, trichloroethoxycarbonyl (Troc), pivaloyl (Piv), allyloxycarbonyl); $C_6$-$C_{10}$-aryl$C_1$-$C_6$-alkoxycarbonyl (e.g. 9-fluorenylmethyloxy carbonyl (Fmoc)); allyl or cinnamyl; sulfonyl or sulfenyl; succinimidyl group, silyl groups (e.g. triarylsilyl, trialkylsilyl, triethylsilyl (TES), trimethylsilylethoxymethyl (SEM), trimethylsilyl (TMS), triisopropylsilyl or tert-butyldimethylsilyl).

As used herein, the term "$C_1$-$C_{12}$alkyl" refers to a straight or branched hydrocarbon chain radical consisting solely of carbon and hydrogen atoms, containing no unsaturation, having from one to twelve carbon atoms, and which is attached to the rest of the molecule by a single bond. The term "$C_1$-$C_6$alkyl" is to be construed accordingly. Examples of $C_1$-$C_{12}$alkyl include, but are not limited to, ethyl, n-propyl, 1-methylethyl (iso-propyl), n-butyl, n-pentyl 1,1-dimethylethyl (tert-butyl).

As used herein, the term "Halogen" or "Halo" refers to bromo, chloro, fluoro or iodo.

The term "about", as used herein, is intended to provide flexibility to a numerical range endpoint, providing that a given value may be "a little above" or "a little below" the endpoint accounting for variations one might see in the measurements taken among different instruments, samples, and sample preparations. The term usually means within 10%, preferably within 5%, and more preferably within 1% of a given value or range.

The term "room temperature" or "ambient temperature" as used herein, unless specified otherwise, means a temperature from 15 to 30° C., such as from 20 to 30° C., particularly such as from 20 to 25° C. The term "internal temperature" as used herein, unless specified otherwise, means the temperature measured inside of the reactor vessel in which the reaction is performed. Such temperature is expressed in degree Celsius. The term "jacket temperature" as used herein, unless specified otherwise, means the temperature measured inside the jacket of the reactor vessel in which the reaction is performed.

The term "stereoisomers" means one of the absolute configurations of a single organic molecule having at least one asymmetric carbon. Also, as used herein, the term refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures.

In the formulae of the present application the term "╱" on a C-sp$^3$ indicates the absolute stereochemistry, either (R) or (S).

In the formulae of the present application the term "╱" on a C-sp$^3$ indicates the absolute stereochemistry, either (R) or (S).

The term "resolution" refers to the separation or concentration or depletion of one of the stereoisomers of a molecule.

The term "seed" can be used as a noun to describe one or more crystals of a crystalline compound of same formula as the final compound of the reaction of interest. The term "seed" can also be used as a verb to describe the act of introducing said one or more crystals of a said crystalline compound into an environment (including, but not limited to, for example, a solution, a mixture, a suspension, or a dispersion) thereby resulting in the formation of more crystals of the final compound.

The term "pharmaceutically acceptable salts" or "salt thereof" refers to salts that can be formed, for example, as acid addition salts, preferably with organic or inorganic acids. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. The salts of the compound of formula (I), and intermediates, as described in the present invention, are preferably pharmaceutically acceptable salts; suitable counter-ions forming pharmaceutically acceptable salts are known in the field. The term "pharmaceutically acceptable" refers to those compounds, materials, compositions, and/or dosage forms which are suitable for use in contact with the tissues of human beings and animals without excessive toxicity, irritation, allergic response, or other problem or complication, commensurate with a reasonable benefit/risk ratio.

The term "additive" as used herein refers to a base, an acid, a ligand, or any other chemical species that can enhanced the reactivity of the reaction.

As used in this specification and the appended claims, the singular forms "a", "an", and "the" include plural referents unless the context clearly indicates otherwise.

Similarly, "comprise", "comprises", "comprising", "include", "includes" and "including" are interchangeable and not intended to be limiting.

Abbreviations

δ Chemical shift
(4-F—$C_6H_4$)$_3$P tris(4-fluorophenyl)phosphine
(Boc)$_2$O di-tert-butyl carbonate
(R)-(+)-MeO-BIPHEP (R)-(+)-(6,6'-Dimethoxybiphenyl-2,2'-diyl)bis(diphenylphosphine)
(R)-segphos (R)-(+)-5,5'-Bis(diphenylphosphino)-4,4'-bi-1,3-benzodioxole
(R,R)-Ph-BPE (+)-1,2-Bis((2R,5R)-2,5-diphenylphospholano)ethane
(S)-BINAP (S)-(2,2'-bis(diphenylphosphino)-1,1'-binaphthyl)
(S)-SDP (S)-(−)-7,7'-Bis(diphenylphosphino)-2,2',3,3'-tetrahydro-1,1'-spirobiindene
(S)-Tol-BINAP (R)-(+)-2,2'-Bis(di-p-tolylphosphino)-1,1'-binaphthyl
(S)-XylBINAP 1,1'-Binaphthalene-2,2'-diylbis[bis(3,5-dimethylphenyl)phosphine]
(S,S)-Et-DUPHOS (+)-1,2-Bis[(2S,5S)-2,5-diethylphospholano]benzene
(S,S)-iPr-DUPHOS (+)-1,2-Bis[(2S,5S)-2,5-diisopropylphospholano]benzene
(S,S)-Me-DUPHOS (+)-1,2-Bis[(2S,5S)-2,5-dimethylphospholano]benzene
(S,S)-Me-Ferrocelane 1,1'-Bis[(2S,5S)-2,5-dimethylphospholano]ferrocene
[Rh(COD)Cl]$_2$ Chloro(1,5-cyclooctadiene)rhodium(I) dimer
[Rh(COD)OMe]$_2$ Methoxy(cyclooctadiene)rhodium(I) dimer
[Rh(MeCN)$_2$(COD)]BF$_4$ Bis(1,5-cyclooctadiene)rhodium (I) tetrafluoroborate
[Rh(OH)((S)-BINAP)]$_2$ Hydroxy[-(S)-BINAP]-rhodium(I) Dimer
[RhCl(S)-BINAP]$_2$ Chloro[(S)-BINAP]-rhodium(I) Dimer
$^1$H-NMR Proton nuclear magnetic resonance
9-BBN 9-borabicyclo(3.3.1)nonyl
acac acetylacetone
alloc allyloxycarbonyl
Boc/Boc$_2$O Tert-butyloxycarbonyl/di-tert-butyl dicarbonate
Br/d/m/t/s/q Broad/doublet/multiplet/triplet/singlet/quadruplet
Bz/Cbz Benzyl/Benzyl chloroformate
CDCl$_3$ Chloroform-deuterated
COD Cyclooctadiene
CPME Cyclopentyl methyl ether
DABCO 1,4-Diazabicyclo[2.2.2]octane
DBU 1,8-Diazabicyclo[5.4.0]undec-7-ene
DEM diethoxymethane
DIPEA N,N-Diisopropylethylamine
DMA Dimethylacetamide
DMAP 4-dimethylaminopyridine
DMF dimethylformamide
DMSO/DMSO-d6 Dimethyl sulfoxide/Dimethyl sulfoxide-deuterated
DPEPhos oxydi-2,1-phenylene)bis(diphenylphosphine
EDTA-4Na.2H$_2$O Tetrasodium dihydrate
ee Enantiomeric excess
eq equivalent
Et$_3$N Triethylamine
Et$_3$SiH Triethylsilane
FAD Flavin adenine dinucleotide
g/mg Gram(s)/milligram(s)
GC Gas chromatography
GDH Glucose dehydrogenase
H$_2$ Dihydrogen
HCl/HF Hydrogen Chloride/Hydrogen fluoride
HEPES 4-(2-hydroxyethyl)-1-piperazineethanesulfonic acid
HPLC High Performance Liquid Chromatography
HRMS High resolution mass spectrometry
Hz/MHz Hertz/Mega Hertz
IT/JT Internal temperature in celsius/Jacket temperature in celsius
J Coupling constant
K$_2$CO$_3$ Potassium carbonate
KRED Ketoreductase
LCMS Liquid chromatography-mass spectrometry
M Molar
MCC Microcrystalline cellulose
mL/L Milliliter(s)/Liter(s)
Mol/mmol Mole(s)/Millimole(s)
MOPS 3-(N-morpholino)propanesulfonic acid
MTBE Methyl tert-butyl ether
N normal
Na$_2$HPO$_4$ Disodium phosphate
NAD Nicotinamide adenine dinucleotide
NADP Nicotinamide adenine dinucleotide phosphate
NaHCO$_3$ Sodium bicarbonate
NaOTf sodium trifluoromethanesulfonate
nbd norbornadiene
NBS/NCS N-bromosuccinimide/N-chlorosuccinimide
NH$_4$Cl/NaCl Ammonium chloride/Sodium chloride
NHC-Pd(II)N-heterocyclic carbene-palladium (II)
PBS Phosphate buffer saline
Pd(O$_2$CCF$_3$)$_2$ Palladium(II) trifluoroacetate
Pd(OAc)$_2$ palladium(II) acetate
Pd/C Palladium on carbon
PIPES piperazine-N,N'-bis(2-ethanesulfonic acid
ppm Parts per million
PTS tocopherol polyethylene glycol succinates
Rh(acac)(C$_2$H$_4$)$_2$ Acetylacetonatobis(ethylene)rhodium(I)
Rh(acac)(COD) (Acetylacetonato)(1,5-cyclooctadiene)rhodium(I)
Rh(COD)BF$_4$ Bis(1,5-cyclooctadiene)rhodium(I) tetrafluoroborate
Rh(nbd)$_2$BF$_4$ Bis(norbornadiene)rhodium(I) tetrafluoroborate
RPM Rotations per minute
TBAI tetrabutylammonium iodide
TBDPS tert-butyldiphenylsilyl
TBS Tert-butyldimethylsilyl
TES/TESOTf Triethylsilyl trifluoromethanesulfonate/triethylsilyl
TFA Trifluoroacetic acid
THF tetrahydrofuran
TIPS triisopropylsilyl
TMS trimethylsilyl
Tosyl Toluenesulfonyl
TPGS Tocopherol polyethylene glycol succinates
TRIS 2-Amino-2-(hydroxymethyl)propane-1,3-diol
v/v volume to volume
Wt % Weight percent Xantphos 4,5-bis(diphenylphosphino)-9,9-dimethylxanthene
XRPD X-ray diffraction pattern

EXAMPLES

The following examples are merely illustrative of the present invention and they should not be considered as limiting the scope of the invention in any way, as these examples, and other equivalents thereof will become apparent to those skilled in the art in the light of the present invention, and the accompanying claims.

Syntheses

The skilled person will appreciate that the general synthetic routes detailed above show common reactions to transform the starting materials as required. When specific reactions are not provided the skilled person will know that such reactions are well known to those skilled in the art and appropriate conditions considered to be within the skilled person's common general knowledge. The starting materials are either commercially available compounds or are known compounds and can be prepared from procedures described in the organic chemistry art.

Compounds as described herein, in free form, may be converted into salt form and vice versa, in a conventional manner understood by those skilled in the art. The compounds in free or salt form can be obtained in the form of hydrates or solvates containing a solvent used for crystallization. Compounds described herein can be recovered from reaction mixtures and purified in a conventional manner. Isomers, such as stereoisomers, may be obtained in a conventional manner, e.g. by fractional crystallization or asymmetric synthesis from correspondingly asymmetrically substituted, e.g. optically active, starting materials. The various starting materials, intermediates, and compounds of the preferred embodiments may be isolated and purified, where appropriate, using conventional techniques such as precipitation, filtration, crystallization, evaporation, distillation, and chromatography. Unless otherwise stated. Salts may be prepared from compounds by known salt-forming procedures.

The compounds described herein can be prepared, e.g. using the reactions and techniques described below and in the examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It would be understood by the skilled person in the art, that the reactions were run on a small scale first in order to access if the starting materials could react in high yields and high purities before to be scalable. The desired compounds obtained during such small scale reaction, that spontaneously crystallized, were used to enhance the latest reactions, using the technique of "seeding". Here below approximately 1% by weight or less of seeding crystals were added, if needed, to the reaction mixture to generate quicker the spontaneous crystallization of the desired product.

Measurements Methods

Proton-NMR: measurements were performed on Bruker 400 Mhz spectrometer. Chemical shifts (δ-values) are reported in ppm downfield and the spectra splitting pattern are designated as singlet (s), doublet (d), triplet (t), quartet (q), quintet (quint), multiplet, unresolved or overlapping signals (m), broad signal (br). Deuterated solvents are given in parentheses.

HPLC: measurements were performed on Agilent 1200 HPLC with high pressure mixing (Column: Waters XBridge BEH C18) and Agilent 1290 UHPLC (Column: Water Acquity BEH C18)

1. C4 CPD method: Agilent 1200 HPLC with high pressure mixing
Solvents: Mobile phase A: 10 mM ammonium acetate in water and Mobile phase B: acetonitrile. This method was used only for compound of formula (C4).

2. 1601 method: Agilent 1290 UHPLC
Solvents: Mobile phase A: 0.05% TFA in water/acetonitrile 95/5 (v/v) and Mobile phase B: 0.05% TFA in water/ACN 5/95 (v/v)

HRMS: Waters ACQUITY UPLC/SYNAPT HDMS QTOF system.

LCMS: Waters ACQUITY UPLC/SYNAPT HDMS QTOF system or Agilent 1290 Infinity/MSD LC/MS system.

XRPD: measurements were performed on Bruker D2 phaser-source CuKα λ=1.5418 Å. One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal forms of the instant invention are not limited to the crystal forms that provide X-ray diffraction patterns completely identical to the X-ray diffraction patterns depicted in the accompanying Figures disclosed herein. Any crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

Example 1: Synthesis of Benzyl-2-[4-(methoxycarbonyl)phenyl]-4-oxopiperidine-1-carboxylate (C4) According to the Following Sequence

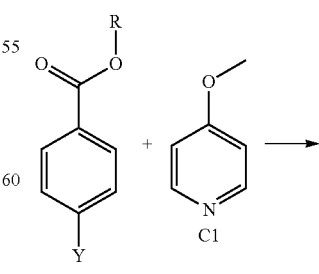

C2
Y = Iodide
R = Methyl

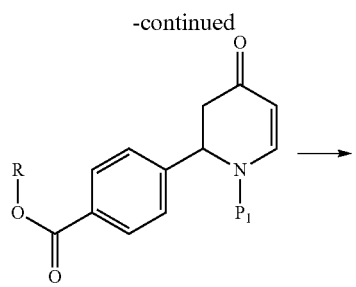

C3
P₁ = Cbz
R = Methyl

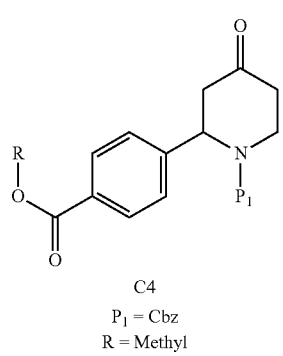

C4
P₁ = Cbz
R = Methyl

Step 1: Synthesis of Benzyl-2-[4-(methoxycarbonyl)phenyl]-4-oxo-3,4-dihydro pyridine-1(2H)-carboxylate (C3, Wherein P₁=Cbz and R=Methyl)

iPrMgCl (2N THF, 109.96 g, 54.98 mL, 2.0 eq) was charged in a reactor. A solution of bis[2-(N,N-dimethylaminoethyl)] ether (2.5 eq, 22.03 g, 137.46 mmol) in THF (24 mL) was added at 15-25° C. The mixture was stirred for 1 hour. A solution of C1 (20.17 g, 76.98 mmol, 1.4 eq) in THF (102 mL) was added slowly at 15-25° C. The mixture was heated to 25-30° C., stirred for more than 1 hour, and checked by HPLC. The mixture was cooled to −30° C. A solution of C2 (methyl 4-iodobenzoate, 6.0 g, 54.98 mmol, 1.0 eq) in THF (20 mL) was added, followed by a solution of benzyl chloroformate (1.15 eq, 10.79 g, 63.23 mmol) in THF (36 mL). The mixture was stirred for 2 hours and quenched with AcOH (6.60 g, 109.96 mmol, 2 eq). Isopropyl acetate (60 mL) was added. Hydrogen chloride (15%, 90 g) was added to adjust the pH=1-2. The organic layer was separated and washed with brine (15%, 100 g), and concentrated. Isopropyl acetate (160 mL) was added and concentrated to remove the THF. The crude product was recrystallized in Isopropyl acetate (114 mL) and n-heptane (120 mL). The product was dried at 60° C. to provide C3 as light yellow solid (16.0 g, 79.65% yield). ¹H-NMR (400 MHz, DMSO-d6) δ (ppm)=8.11 (dd, J=8.39, 1.01 Hz, 1H), 7.91 (d, J=8.39 Hz, 2H), 7.33-7.37 (m, 6H), 5.82 (d, J=7.20 Hz, 1H), 5.20-5.35 (m, 3H), 3.83 (s, 3H), 3.41 (br. s, 1H), 3.31 (dd, J=16.64, 7.52 Hz, 1H), 2.66 (br. d, J=16.55 Hz, 1H).

Step 2: Synthesis of Benzyl-2-[4-(methoxycarbonyl)phenyl]-4-oxopiperidine-1-carboxylate (C4, Wherein P₁=Cbz and R=Methyl)

A solution of C3 (25 g, 68.42 mmol, 1.0 eq) in AcOH (200 mL) was heated to 50-60° C. to form a clear solution. The solution was then cooled to 35° C. Zn powder (13.42 g, 205.26 mmol, 3.0 eq) was added portionwise while keeping the inner temperature at 35-40° C. After addition, the mixture was stirred for more than 8 hours and checked by HPLC. THF (250 mL) was added. The mixture was cooled to 25° C., filtered, and the filter cake was washed with THF (125 volume). The filtrate was concentrated to dryness. Isopropanol (375 mL) was added. The solution was cooled to 0-5° C. EDTA-4Na.2H₂O (40 g) in water (200 mL) was added. The mixture was neutralized to pH=9-10 with 30% sodium hydroxide solution and stirred for 2 hours. The organic layer was collected, washed with brine (15%, 250 g) and concentrated to about 50 mL. MTBE (100 mL) was added and concentrated to about 50 mL. MTBE (80 mL) was added followed by n-heptane (20 mL) dropwise. Then the mixture was cooled to 0° C. gradually. The mixture was filtered and the filter cake was dried to afford C4 as a light yellow solid (20.11 g, 80.0% yield). ¹H NMR (400 MHz, CDCl₃) δ (ppm)=7.99 (d, J=8.31 Hz, 2H), 7.27-7.39 (m, 7H), 5.83 (br. s, 1H), 5.14-5.28 (m, 2H), 4.20-4.42 (m, 1H), 3.92 (s, 3H), 3.12-3.33 (m, 1H), 2.84-3.04 (m, 2H), 2.46-2.65 (m, 1H), 2.23-2.45 (m, 1H).

Example 2: Synthesis of Benzyl (4S)-4-hydroxy-2-(4-(methoxycarbonyl)phenyl)piperidine-1-carboxylate (C5, Wherein P₁=Cbz and R=Methyl)

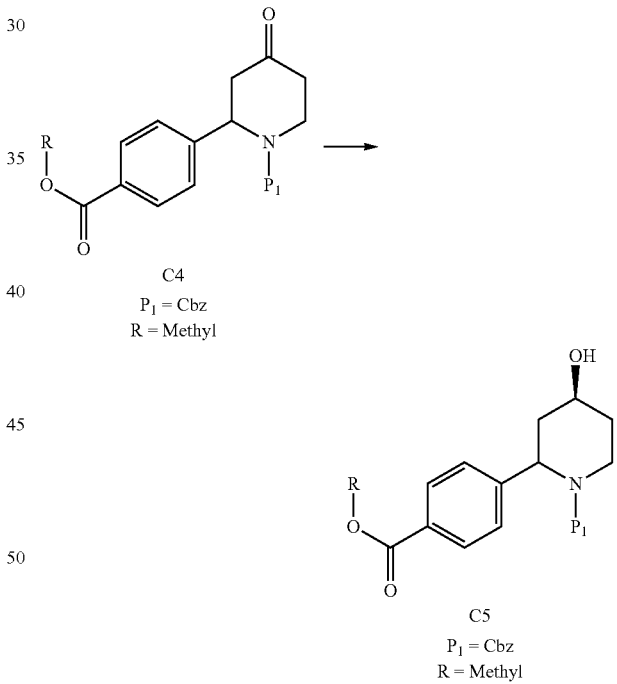

C4
P₁ = Cbz
R = Methyl

C5
P₁ = Cbz
R = Methyl

A 0.1 M pH=7.0 PBS was prepared with disodium phosphate dodecahydrate (22.2 g), sodium dihydrogen phosphate dihydrate (6.2 g) and purified water (999 g). To a reactor equipped with a pH meter 0.1 M pH=7.0 PBS (499 g), D-glucose (40.2 g, 233.14 mmol, 2.0 eq), NADP (EnzymeWorks, 0.72 g), GDH (EnzymeWorks, 0.41 g) and KRED-EW124 (EnzymeWorks, 2.05 g) were added, followed by addition of emulsion of C4 (41 g, 111.60 mmol, 1.0 eq) in DMSO (102.5 mL). The mixture was heated to JT≤45° C., IT 41±3° C. and stirred at IT 41±3° C. for ≥16 h while controlling pH 6.9-7.2 by adding 1M sodium hydroxide solution. A mixture of NADP (0.29 g), GDH (0.16 g) and KRED-EW124 (0.82 g, #Enzyme Works Inc. China) in 0.1 M pH=7.0 PBS (11 g) were charged and stirred at IT 41±3° C. for ≥20 hours. The reaction was monitored by HPLC. The reaction was filtered to afford white wet cake. To a 1.0 L Radleys reactor equipped with anchor agitator crude C5 wet cake (80 g) and acetonitrile (500 mL) were charged. The mixture was stirred to form a light yellow suspension (700 RPM). The suspension was heated to IT=70±5° C. and stirred for 4 hours, and then cooled to IT=25±5° C. The suspension was filtered and the cake was washed with acetonitrile (75 mL). To a clean 500 mL Radleys reactor equipped with anchor agitator the resulting mother liquor was charged. The mother liquid was concentrated to about 95 g, solvent exchanged with three portions of toluene (105 g) to 95 g residue. Toluene (170 g) was charged and the reaction was checked by GC (acetonitrile/(toluene+acetonitrile)≤1.2%). The suspension was heated to IT=80±5° C., held for 1 hour, cooled to IT=45±3° C. and adjusted the agitation speed to low mode. Sequential operations of seeding and aging for 2 hours, charging n-heptane (10.2 g) in 0.5 hours and aging for 1 hour, charging n-heptane (34 g) over 1.5 hours and aging for 0.5 hours were carried out. The mixture was cooled to IT=10±3° C. over 7 hours and maintained at 10±3° C. for 2 hours. The mixture was filtered and the cake was washed with cold mixed solvents of toluene (50 mL) and n-heptane (10 mL) to afford a light yellow solution of C5 (330 g, trans/cis=90/10, assay 6.8%, yield 52%). The mother liquor was telescoped to the next step. $^1$H-NMR (400 MHz, CDCl$_3$, mixture of two isomers, data for the minor isomer is shown in brackets): δ (ppm)=7.99 (d, J=8.44 Hz, 2H) [7.92 (d, J=8.44 Hz, 0.04H)], 7.23-7.39 (m, 7H) [7.10-7.18 (m, 0.21H)], 5.69 (br. s, 1H) [5.40-5.42 (m, 0.11H)], 5.19 (s, 2H) [5.14 (s, 0.23H)], 4.26 (br. d, J=13.33 Hz, 1H) [4.18-4.20 (m, 0.13H)], 3.91 (s, 3H) [3.90 (s, 0.4H)], 3.67-3.79 (m, 1H) [3.38-3.45 (m, 0.11H)], 2.83 (td, J=13.51, 2.81 Hz, 1H), 2.64 (br. d, J=13.33 Hz, 1H) [2.41-2.47 (m, 0.12H)], 1.81-1.91 (m, 2H) [2.17-2.22 (m, 0.12H)], 1.72-1.77 (m, 1H), 1.45-1.56 (m, 1H). HRMS: Calcd for C$_{21}$H$_{24}$NO$_5$ (M+H): 370.1654m, found 370.1662.

Example 3: Synthesis of Methyl 4-[(2S,4S)-4-ethoxypiperidin-2-yl]benzoate (Compound of Formula (II)) According to the Following Sequence

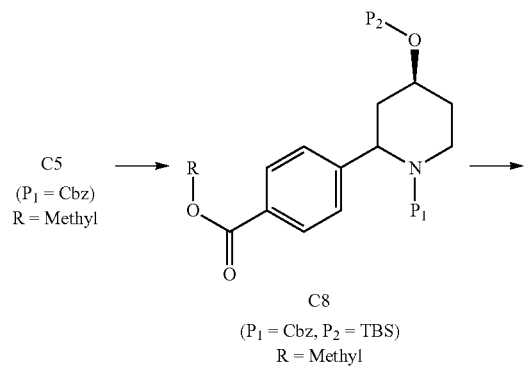

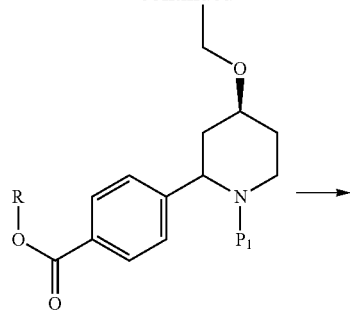

C9
(P$_1$ = Cbz)
R = Methyl

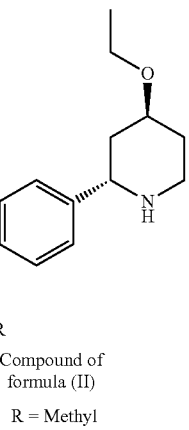

Compound of formula (II)
R = Methyl

Step 1: Synthesis of Benzyl (4S)-4-((tert-butyldimethylsilyl)oxy)-2-(4-(methoxycarbonyl) Phenyl)piperidine-1-carboxylate (C8, Wherein P$_1$=Cbz, P$_2$=TBS and R=Methyl)

To a 500 mL Radleys Reactor charged with C5 in a toluene/heptane solution (1.0 eq, 145.67 g from previous step, assay 6.07%, 23.94 mmol). The solution was concentrated to about 25 g. Then dichloromethane (117.1 g) was charged and the solution was cooled to 23±4° C. To the clear solution, imidazole (3.42 g, 50.26 mmol, 2.1 eq) and TBS-Cl (6.13 g, 40.69 mmol, 1.7 eq) were introduced. The yellow suspension was stirred at 23±4° C. for 10 hours. The reaction was monitored by HPLC. Then 10% Na$_2$CO$_3$ (70.7 g) was charged and the mixture was stirred for 1 hours. The organic phase was washed with 5% brine (53 g) and concentrated to about 30 g. Then the solvent was exchange with toluene (45 g) to about 25 g. The residue was diluted with dichloromethane (66 g) and the mixture was filtered through a pad of 200-300 mesh silica gel (1.66 g). The silica gel was eluted with another portion of dichloromethane (17.5 g). The eluent was concentrated and the residue was subjected to solvent exchange with acetonitrile (71.1 g+98.2 g) to 90 g (yield 100%). C8 in acetonitrile solution was used in the next step. $^1$H-NMR (400 MHz, CDCl$_3$, mixture of two isomers, data for the minor isomer is shown in brackets): δ (ppm)=8.01 (d, J=8.44 Hz, 2H) [7.94 (d, J=8.44 Hz, 0.17H)], 7.26-7.34 (m, 7H) [7.09-7.18 (m, 0.13H)], 5.65 (br. d, J=2.04 Hz, 1H) [5.41 (br. d, J=2.04 Hz, 0.08H)], 5.19 (s, 2H) [5.13 (s, 0.16H)], 4.22 (br. d, J=13.69 Hz, 1H) [4.10-4.14 (m, 0.19H)], 3.92 (s, 3H) [3.90 (s, 0.3H)], 3.62-3.69 (m, 1H) [3.43-3.50 (m, 0.08H)], 2.81 (td, J=13.54, 2.87 Hz, 1H), 2.49

(br. d, J=13.57 Hz, 1H) [2.31-2.35 (m, 0.10H)], 1.84-1.92 (m, 1H) [2.08-2.14 (m, 0.07H)], 1.74-1.75 (m, 1H), 1.48-1.59 (m, 1H), 0.86 (s, 9H) [0.56 (s, 0.65H)], 0.03 (s, 3H) [0.09 (s, 0.27H)].

Step 2: Synthesis of Benzyl (4S)-4-ethoxy-2-(4-(methoxycarbonyl)phenyl)piperidine-1-carboxylate (C9, Wherein $P_1$=Cbz, R=Methyl)

To a 250 mL Radleys Reactor equipped with impeller agitator C8 in acetonitrile solution (135.5 g, assay 12.53%, 35.10 mmol) was charged and rinsed with acetonitrile (with 8.5 g). $Et_3SiH$ (12.25 g, 105.31 mmol, 3.0 eq) was charged. The reactor was cooled to IT=4±5° C. TESOTf (1.392 g, 5.265 mmol, 0.15 eq) was charged. A solution of 2,4,6-trimethyl-1,3,5-trioxane (4.64 g, 35.10 mmol, 1.0 eq) in acetonitrile (7.9 g) was added to the mixture in 60 min at IT=4±5° C. After addition, the mixture was stirred for 15 min and followed by HPLC. To the reaction mixture was charged 5% aqueous $Na_2CO_3$ (21.22 g) and water (30 g). Followed by n-heptane (20.4 g) and the mixture was stirred at 25±5° C. for 30 min. Phase cut and the bottom acetonitrile phase was collected. The acetonitrile phase was concentrated to about 65 g. MTBE (100.6 g) and 5% aqueous $Na_2CO_3$ (43.44 g) were charged to the residual acetonitrile solution. The mixture was stirred for 30 min. The upper MTBE phase was collected and filtered via Charcoal film. The charcoal film was washed with MTBE (7.4 g). The mother liquor was concentrated to about 35 g. To the residue methanol (79.2 g) was charged and the solution was concentrated to 70 g. The solution was telescoped to the next step. $^1$H NMR (400 MHz, $CDCl_3$, mixture of two isomers, data for the minor isomer is shown in brackets) δ (ppm) =8.01 (d, J=8.31 Hz, 2H) [7.96 (d, J=8.31 Hz, 0.21H)], 7.29-7.32 (m, 7H) [7.07-7.22 (m, 0.40H)], 5.68 (br. s, 1H) [5.32-5.34 (m, 0.10H)], 5.19 (s, 2H) [5.11 (s, 0.19H)], 4.27 (br. d, J=13.08 Hz, 1H) [4.05-4.14 (m, 0.15H)], 3.91 (s, 3H) [3.89 (s, 0.15H)], 3.41-3.54 (m, 2H) [3.14-3.25 (m, 0.21)], 3.30-3.40 (m, 1H) [3.86-3.75 (m, 0.13H)], 2.84 (td, J=13.51, 2.81 Hz, 1H), 2.66 (br. d, J=13.20 Hz, 1H), 1.62-1.95 (m, 2H), 1.40-1.53 (m, 1H), 1.18 (t, J=6.97 Hz, 3H).

Step 3: Synthesis of Methyl 4-((4S)-4-ethoxypiperidin-2-yl)benzoate (Removal of the Protecting Group $P_1$=Cbz-R=Methyl)

To a 500 mL autoclave charged with 10% Pd/C (50% wet, 3.83 g), C9 solution in methanol (assay 19.97%, 192 g, 96.46 mmol) and methanol (28 g). The reactor was purged with vacuum/$H_2$, three times. The mixture was hydrogenated at 3 bar and at a temperature of 25±4° C. for 4 hours. The mixture was filtered and the Pd/C cake was washed with methanol (20 g). The mother liquor was concentrated to 48 g, solvent swapped twice with 142 g isopropyl acetate to 106 g, cooled to 8±5° C., and 3% hydrogen chloride solution (90.2 g) was added. After phase separation, the aqueous phase was collected and washed with isopropyl acetate (86.4 g). To the aqueous phase MTBE (72 g) and 10% $Na_2CO_3$ (99.2 g) were added. After phase separation, the aqueous phase was extracted with MTBE (72 g). The combined MTBE phase was washed with water (40 g). The MTBE solution was introduced into the next step. $^1$H NMR (400 MHz, $CDCl_3$, mixture of two isomers, data for the minor isomer is shown in brackets) δ (ppm)=7.96 (m, J=8.31 Hz, 2H), 7.40-7.46 (m, 2H), 4.06 (dd, J=11.62, 2.45 Hz, 1H), 3.88 (s, 3H), 3.70-3.79 (m, 1H) [3.64-3.69 (m, 0.12H)], 3.48-3.56 (m, 2H) [3.38-3.45 (m, 0.11H)], 3.11-3.18 (m, 1H) [3.21-3.26 (m, 0.11H)], 2.88-2.97 (m, 1H) [2.73-2.80 (m, 0.12H)], 1.94-2.00 (m, 1H) [2.14-2.19 (m, 0.10H)], 1.84-1.89 (m, 1H) [2.02-2.07 (m, 0.12H)], 1.75 (S, 1H), 1.65-1.70 (m, 1H) [1.45-1.49 (m, 0.10H)], 1.59-1.64 (m, 1H) [1.36-1.42 (m, 0.11H)], 1.22-1.25 (t, 3H) [1.17-1.20 (t, J=6.97, 0.24H)].

Step 4: Synthesis of Methyl 4-[(2S,4S)-4-ethoxypiperidin-2-yl]benzoate (Compound of Formula (II)—R=Methyl)

To a 500 mL one neck flask was added the crude solution of step 3 (above) in MTBE (telescoped from last step, 110 g, assay 10.52%, light yellow solution, 43.95 mmol). The solution was concentrated to 18.4 g and the solvent was exchanged (JT=60° C.) with 55 g of n-heptane twice to get 35 g yellow solution. The solution was transferred to 100 mL Easy Max equipped with impeller agitator. The solution was heated to 50° C. with 300 RPM, aged for 30 min, cooled to 41±2° C. and seed was added. The agitation was adjusted to low speed. The mixture was aged at 41±2° C. for 2 hours, cooled to 35±2° C. in 8-10 hours and then aged at 35±2° C. for 1-2 hours. n-heptane (7.9 g) was added dropwise. The agitation was adjusted to medium speed. The mixture was cooled to IT=25±2° C. in 1 hour and aged at 25±2° C. for 10-20 minutes. The mixture was filtered. The filtrate was re-charged to the reactor for rinsing the solid on the reactor wall. The mixture was filtered and the filter cake was washed with pre-cooled (−5° C.) n-heptane (7.9 g). The cake was dried at 40° C. for 10 hours to afford 6.4 g of white solid (50% yield). $^1$H NMR (400 MHz, $CDCl_3$) δ (ppm)=7.99 (m, J=8.31 Hz, 2H), 7.45 (m, J=8.19 Hz, 2H), 4.09 (dd, J=11.62, 2.20 Hz, 1H), 3.90 (s, 3H), 3.75 (t, J=2.81 Hz, 1H), 3.53 (q, J=6.97 Hz, 2H), 3.17 (td, J=12.13, 2.63 Hz, 1H), 2.91-2.99 (m, 1H), 1.99 (dd, J=13.57, 2.69 Hz, 1H), 1.88 (dt, J=13.79, 2.58 Hz, 1H), 1.69-1.79 (m, 1H), 1.57-1.68 (m, 2H), 1.25 (t, J=7.03 Hz, 3H).

Example 4: Enantioselective Synthesis of Compound (S)-(C4) According to the Following Sequence

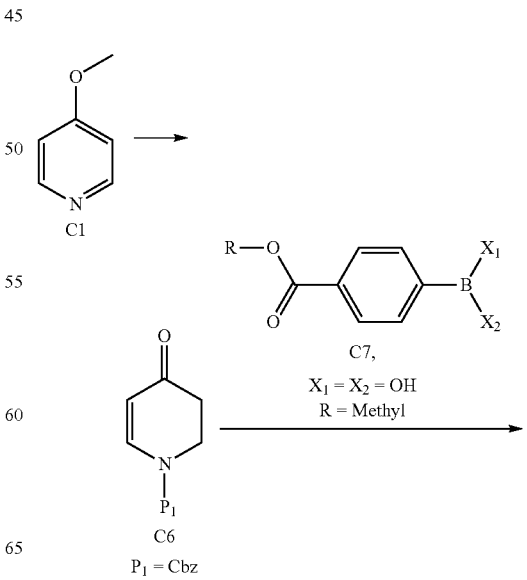

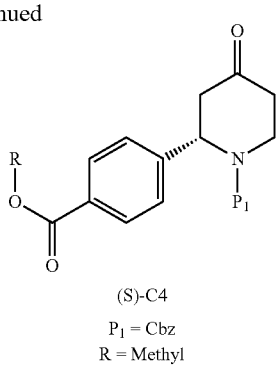

(S)-C4
P₁ = Cbz
R = Methyl

Step 1: Synthesis of Benzyl 4-oxo-3,4-dihydropyridine-1(2H)-carboxylate (C6, Wherein P₁=Cbz and R=Methyl)

To a 2.0 L reactor, 4-methoxypyridine (C1, 45.0 g, 412.39 mmol, 1.0 eq) and methanol (900 mL) were added. The mixture was cooled to −75° C. with dry ice/acetone bath. A solution of benzyl chloroformate (73.86 g, 432.99 mmol, 1.05 eq) in THF (90 mL) was charged dropwise while keeping IT≤−70° C. The reaction was stirred for 1 hour to afford a white suspension at −70° C. Sodium borohydride (16.38 g, 432.99 mmol, 1.05 eq) was added in portions while keeping IT≤−70° C. The reaction was stirred at −70° C. for 2 hours. Water (200 g) was added and the cooling bath was removed. A solution of 36% hydrogen chloride (16.72 g, 164.95 mmol, 0.4 eq) in water (50 mL) was added in 10 min at 0-5° C. and stirred for 1 hour. Then 20% Na₂CO₃ (85.5 g) was added to adjust pH=7 while maintained IT≤5° C. Organic solvents were removed under vacuum. The resulting residue was extracted with dichloromethane (450 mL). The dichloromethane phase was washed with 3 wt % hydrogen chloride (151 mL) and 3 wt % Na₂CO₃ (151 mL). After solvent exchange with MTBE, about 4 volume (180 ml) of the MTBE mixture was obtained. The mixture was heated to 50° C. to afford a solution and then cooled to 45° C. Crystal seed of C6 was charged and the mixture was aged at 40-45° C. for 7 hours. The mixture was cooled to 10-15° C. in 3 hours. The white suspension was filtered and the wet cake was rinsed with cold MTBE (45 mL). The cake was dried under vacuum at 40-50° C. for 2 hours to afford C6 as a white powder (91.56 g, 60% yield). $^1$H NMR (400 MHz, CDCl₃): δ (ppm)=7.85 (br. s, 1H), 7.37-7.43 (m, 5H), 5.43 (br. s, 1H), 5.26 (s, 2H), 4.05 (t, J=7.34 Hz, 2H), 2.54-2.58 (m, 2H).

Step 2: Synthesis of Benzyl (S)-2-(4-(methoxycarbonyl)phenyl)-4-oxopiperidine-1-carboxylate ((S)-C4, Wherein P₁=Cbz and R=Methyl)

Method 1: A 500 ml Radleys reactor was purged 3 times with vacuum/N₂. C6 (8 g, 34.60 mmol, 1.0 eq), C7 (9.34 g, 51.89 mmol, 1.5 eq), tert-Amyl alcohol (160 mL) and deionized water (16 mL) were added. The mixture was stirred for ≥40 minutes to give a clear colorless solution. The solution was purged 4 times with vacuum/N₂ and bubbled with N₂ via a syringe needle for 1 hour. To the colorless solution, was charged the mixed solid of (S)-XylBINAP (0.381 g, 0.519 mmol, 0.015 eq) and Rh(Acac)(C₂H₄)₂ (0.134 g, 0.519 mmol, 0.015 eq). The mixture was continued to bubble with N₂ for 15 minutes and purged 4 times with vacuum/N₂. The suspension was stirred for another 2 hours to dissolve (S)-XylBINAP. The reaction mixture was stirred at 55±4° C. for 15 hours. The reaction was followed by HPLC. The mixture was cooled and treated with 7.7% sodium hypochlorite (1 g, 1.04 mmol, 0.03 eq) for 1.5 hours at 40±4° C. tert-Amyl alcohol was distilled off. The residue was extracted with isopropyl acetate (64 mL) and ethyl acetate (8 mL) and filtered. The organic phase was washed with 5% NaHCO₃ (50 g) then with 15% brine (40 g) at 50±5° C. Some solvents were removed and ethyl acetate (21.6 g) was added. The solution was treated with Smopex-234 (1.2 g) at IT=55±5° C. for 2 hours then filtered via 200-300 mesh silica gel (1.6 g). After solvent exchange with n-heptane, MTBE (44.4 g) was added. The mixture was cooled to IT=42±3° C. (S)-C4 seed (10 mg) was added. The mixture was aged for 2 hours and cooled to IT=31±3° C. in 3 hours. n-heptane (23.2 g) was then charged in 1-2 hours. The mixture was aged for 2 hours and cooled to IT=20±3° C. in 2 hours. The mixture was filtered and the cake was washed with a mixed solvent of MTBE (4.4 g) and n-heptane (4.1 g). Dried the wet cake at 60° C. for 5 hours to afford (S)-C4 (7.63 g, 60% yield) as yellow powder. $^1$H NMR (400 MHz, CDCl₃): δ (ppm)=7.99 (d, J=8.44 Hz, 2H), 7.28-7.37 (m, 7H), 5.82 (br. s, 1H), 5.14-5.28 (m, 2H), 4.30 (br. s, 1H), 3.91 (s, 3H), 3.22 (br. d, J=8.31 Hz, 1H), 2.84-3.03 (m, 2H), 2.46-2.64 (m, 1H), 2.38 (br. d, J=16.26 Hz, 1H).

Method 2: To a 500 ml Radleys reactor purged 3 times with vacuum/N₂, C6 (8 g, 34.60 mmol, 1.0 eq), C7 (9.34 g, 51.89 mmol, 1.5 eq), tert-Amyl alcohol (160 mL) and deionized water (16 mL) were added. The mixture was stirred for roughly 40 minutes to give a clear colorless solution. The solution was purged 4 times with vacuum/N₂ and bubbled with N₂ via a syringe needle for 1 hour. To the colorless solution, was charged the mixed solid of (R,R)-Ph-BPE-Rh(Acac) (0.005 eq., 0.122 g, 0.173 mmol). The mixture was continued to bubble with N₂ for 15 minutes and purged with vacuum/N₂. The reaction mixture was stirred at 55±4° C. for 15 hours. The reaction was followed by HPLC. Tert-amyl alcohol was distilled off. The residue was extracted with isopropyl acetate (64 mL) and ethyl acetate (8 mL), and then filtered. The organic phase was washed with 5% NaHCO₃ (50 g), then with 15% brine (40 g) at 50±5° C. Some solvents were removed and ethyl acetate (21.6 g) was added. The solution was treated with Smopex-234 (1.2 g) at IT=55±5° C. for 2 hours then filtered via 200-300 mesh silica gel (1.6 g). After solvent exchange with n-heptane, MTBE (44.4 g) was added. The mixture was cooled to IT=42±3° C. (S)-C4 seed (10 mg) was added. The mixture was aged for 2 hours and cooled to IT=31±3° C. in 3 hours. n-heptane (23.2 g) was then charged in 1-2 hours. The mixture was aged for 2 hours and cooled to IT=20±3° C. in 2 hours. The mixture was filtered and the cake was washed with a mixed solvent of MTBE (4.4 g) and n-heptane (4.1 g). The wet cake was dried at 60° C. for roughly 5 hours to afford (S)-C4 (10.17 g, 80% yield) as yellow powder. $^1$H NMR (400 MHz, CDCl₃) δ (ppm)=7.99 (d, J=8.44 Hz, 2H), 7.28-7.37 (m, 7H), 5.82 (br. s, 1H), 5.14-5.28 (m, 2H), 4.30 (br. s, 1H), 3.91 (s, 3H), 3.22 (br. d, J=8.31 Hz, 1H), 2.84-3.03 (m, 2H), 2.46-2.64 (m, 1H), 2.38 (br. d, J=16.26 Hz, 1H).

Method 3: To a 500 ml Radleys reactor purged 3 times with vacuum/N₂. C6 (8 g, 34.60 mmol, 1.0 eq), C7 (9.34 g, 51.89 mmol, 1.5 eq), tert-amyl alcohol (160 mL) and deionized water (16 mL) were added. The mixture was stirred for roughly 40 minutes to give a clear colorless solution. The solution was purged 4 times with vacuum/N₂, and bubbled with N₂ via a syringe needle for 1 hour. To the colorless solution was charged the mixed solid of (S)-XylBINAP-Rh(Acac) (0.01 eq., 0.324 g, 0.346 mmol). The mixture was continued to bubble with N₂ for 15 minutes and purged with vacuum/N₂. The reaction mixture was stirred at 55±4° C. for 15 hours. The reaction was followed by HPLC. Tert-amyl alcohol was distilled off. The residue was extracted with isopropyl acetate (64 mL) and ethyl acetate (8 mL), and then filtered. The organic phase was washed with 5% NaHCO₃ (50 g), then with 15% brine (40 g) at 50±5° C. Some solvents were removed and ethyl acetate (21.6 g) was added. The solution was treated with Smopex-234 (1.2 g) at IT=55±5° C. for 2 hours then filtered via 200-300 mesh silica gel (1.6 g). After solvent exchange with n-heptane, MTBE (44.4 g) was added. The mixture was cooled to IT=42±3° C. (S)-C4 seed (10 mg) was added. The mixture was aged for 2 hours and cooled to IT=31±3° C. in 3 hours. n-heptane (23.2 g) was then charged in 1-2 hours. The mixture was aged for 2 hours and cooled to IT=20±3° C. in 2 hours. The mixture was filtered, and the cake was washed with a mixed solvent of MTBE (4.4 g) and n-heptane (4.1 g). The wet cake was dried at 60° C. for roughly 5 hours to afford (S)-C4 (10.30 g, 81% yield) as yellow powder. ¹H NMR (400 MHz, CDCl₃) δ (ppm)=7.99 (d, J=8.44 Hz, 2H), 7.28-7.37 (m, 7H), 5.82 (br. s, 1H), 5.14-5.28 (m, 2H), 4.30 (br. s, 1H), 3.91 (s, 3H), 3.22 (br. d, J=8.31 Hz, 1H), 2.84-3.03 (m, 2H), 2.46-2.64 (m, 1H), 2.38 (br. d, J=16.26 Hz, 1H).

Example 5: Synthesis of Benzyl (2S,4S)-4-hydroxy-2-(4-(methoxycarbonyl)phenyl)piperidine-1-carboxylate ((S)-C5, Wherein P₁=Cbz and R=Methyl)

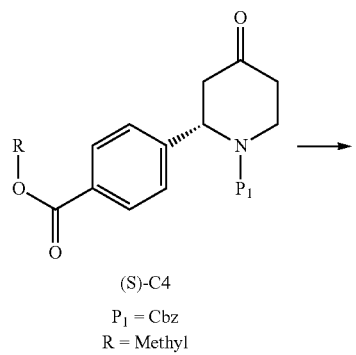

(S)-C4
P₁ = Cbz
R = Methyl

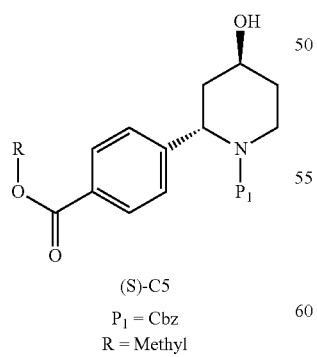

(S)-C5
P₁ = Cbz
R = Methyl

Preparation of 0.1 M PBS, pH 7.0, with 0.1% TPGS buffer solution: To a 500 mL Radleys reactor equipped with impeller agitator was charged Na₂HPO₄.12H₂O (8.63 g), NaH₂PO₄.2H₂O (2.41 g), Tap Water (388.6 g) and TPGS-750-M.001 (0.388 g). The mixture was stirred for ≥3 hours at IT=60±5° C. and then cooled to IT=51±3° C. 80 g of the buffer solution was taken from the reactor to a flask and cooled to ≤35° C. Check pH value of the buffer solution (7.0±0.5). To the above Radleys reactor (S)-C4 (20.0 g, 54.4 mmol, 1.0 eq), Isopropanol (16.36 g, 272.2 mmol, 5.0 eq) and 0.1% TPGS buffer solution (60 g) were added. To a 25 mL flask was charged KRED-P3-G09 (0.4 g, #Codexis), NADP+ (0.1 g) and 0.1% TPGS buffer solution (60 g) from the above flask. All the solid was dissolved. The solution of enzyme was charged to the 500 mL Reactor at IT=50±5° C. Rinsed the 25 mL flask with 0.1% TPGS buffer (10 g) and transferred the solution to the 500 mL reactor at IT=50±5° C. The mixture was stirred with agitation speed 500 RPM at 51±3° C. for ≥8 hours. The reaction was followed by HPLC. To the reactor 2-MeTHF (200 mL) was added and the mixture was stirred for ≥60 minutes at 50±5° C. The mixture was held for ≥50 minutes without agitation and the bottom aqueous phase was separated. The organic phase was washed twice with another 200 g of water at 50±5° C. The organic phase was concentrated to about 70 g. After solvent exchange with twice 158 g acetonitrile to give about 80 g solution, which was cooled to <30° C. then filtered via MCC. MCC cake was washed with isopropyl acetate (40 mL/35.5 g) to afford (S)-05 in a light color solution (114.3 g, assay 16.95% 96.34% yield). The acetonitrile/isopropyl acetate solution was telescoped to the next step directly. ¹H NMR (400 MHz, CDCl₃): δ (ppm)=7.98 (d, J=8.44 Hz, 2H), 7.23-7.38 (m, 7H), 5.61-5.72 (m, 1H), 5.18 (s, 2H), 4.23 (br. d, J=13.33 Hz, 1H), 3.90 (s, 3H), 3.62-3.75 (m, 1H), 2.81 (td, J=13.51, 2.81 Hz, 1H), 2.62 (br. d, J=13.33 Hz, 1H), 2.45 (br. s, 1H), 1.79-1.91 (m, 2H), 1.41-1.56 (m, 1H).

Example 6: Asymmetric Synthesis of Methyl 4-[(2S,4S)-4-ethoxypiperidin-2-yl]benzoate (Compound of Formula (II), or a Salt Thereof, —R=Methyl) According to the Following Sequence

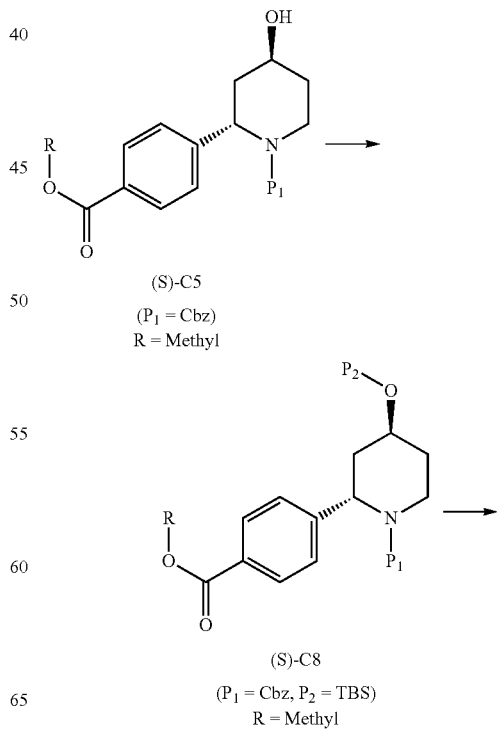

(S)-C5
(P₁ = Cbz)
R = Methyl (S)-C8
(P₁ = Cbz, P₂ = TBS)
R = Methyl

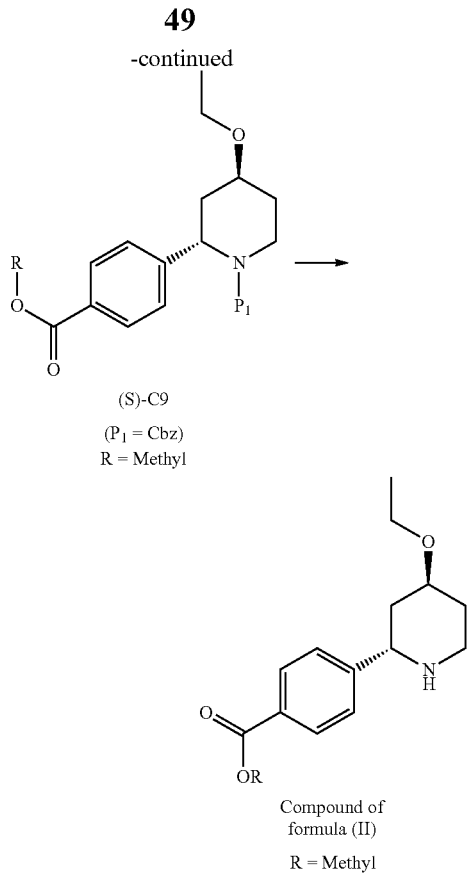

(S)-C9
(P₁ = Cbz)
R = Methyl

Compound of formula (II)
R = Methyl

Step 1: Synthesis of Benzyl (2S,4S)-4-{[tert-butyl (dimethyl)silyl]oxy}-2-[4-(methoxy carbonyl) Phenyl]piperidine-1-carboxylate ((S)-(C8), Wherein P₁=Cbz, P₂=TBS, and R=Methyl)

To a 500 ml Radleys Reactor was charged with (S)-05 solution (in acetonitrile/isopropyl acetate, 271.8 g, assay 14.72%, contained 40.0 g of (S)-05, 108.31 mmol, 1.0 eq) from the previous step. After solvent exchange with isopropyl acetate (159.8 g/180 mL), 100 g clear solution was obtained. Isopropyl acetate (176 g/198 mL), imidazole (26.54 g, 389.90 mmol, 3.6 eq) and TBS-Cl (27.75 g, 184.12 mmol, 1.7 eq) were added. The yellow suspension was stirred at 55±4° C. for 7 hours. The reaction was followed by HPLC. The reaction mixture was cooled to 23±4° C. and filtered through MCC (2 g). The cake was washed with isopropyl acetate (88.8 g/100 mL). 6% NaHCO₃ (240 g) was added and the mixture was stirred for 20 minutes. The organic phase was washed with 5% brine (2×240 g) and concentrated to about 105 g. After solvent exchange with toluene (120 g/135.4 mL), 105 g solution was obtained. Dichloromethane (298 g/224.5 mL) was added and the solution was filtered via 200-300 mesh silica gel (4.4 g). The silica gel was eluted with another portion of dichloromethane (44 g/33 mL). The mother liquor was concentrated and the solvent was exchanged with acetonitrile (2×280 mL, 442.4 g in total) to 100 g. The residue was diluted with acetonitrile (105 g/132.9 mL) to afford a light yellow solution (205 g, assay 25.55%, 100% yield), which was used for the next step directly. ¹H NMR (400 MHz, CDCl₃) δ (ppm)=8.01 (d, J=8.44 Hz, 2H), 7.23-7.37 (m, 7H), 5.60-5.70 (m, 1H), 5.18 (s, 2H), 4.22 (br. d, J=13.45 Hz, 1H), 3.90 (s, 3H), 3.62-3.71 (m, 1H), 2.82 (td, J=13.51, 2.81 Hz, 1H), 2.49 (br. d, J=13.45 Hz, 1H), 1.83-1.96 (m, 1H), 1.75-1.80 (m, 1H), 1.47-1.60 (m, 1H), 0.86 (s, 9H), 0.03 (s, 3H), 0.00 (s, 3H).

Step 2: Synthesis of Benzyl (2S,4S)-4-ethoxy-2-[4-(methoxycarbonyl)phenyl]piperidine-1-carboxylate ((S)-C9, Wherein P₁=Cbz and R=Methyl)

To a 500 mL Radleys Reactor equipped with impeller agitator (S)-C8 in an acetonitrile solution (170.8 g, assay 29.28%, 103.38 mmol, 1.0 eq) and fresh acetonitrile (220 g) were charged, followed by Et₃SiH (36.06 g, 310.13 mmol, 3.0 eq). The mixture was cooled to IT=4±5° C. and TESOTf (5.47 g, 20.68 mmol, 0.2 eq) was charged. To the mixture was charged a solution of 2,4,6-trimethyl-1,3,5-trioxane (13.66 g, 103.38 mmol, 1.0 eq) in acetonitrile (23 g) over 60 minutes at IT=4±5° C. Upon addition, the mixture was stirred for 15 minutes. The reaction was followed by HPLC. To the reaction mixture was charged 5% aqueous sodium hydroxide (16.54 g, 20.68 mmol, 0.2 eq) and 20 g water, followed by n-heptane (60 g). The mixture was stirred for 30 minutes at 20±5° C. The bottom acetonitrile phase was collected. To the acetonitrile phase was charged with MTBE (111 g) and 10% brine (300 g). The mixture was stirred for 30 minutes. The upper MTBE phase was washed with 10% brine (2×300 g), concentrated to 90 g. MTBE (185 g) and water (150 g) were charged. After phase separation at 38±4° C. and solvent exchange of the organic layer with isopropyl acetate (2×266.4 g), 205 g solution was obtained, which was filtered through Charcoal film slowly. The charcoal film was washed with isopropyl acetate (22.2 g) to afford as a light yellow solution (223 g, 100% yield). The solution was telescoped to the next step directly. ¹H NMR (400 MHz, CDCl₃) δ (ppm)=8.01 (d, J=8.44 Hz, 2H), 7.25-7.38 (m, 7H), 5.68 (br. s, 1H), 5.19 (s, 2H), 4.27 (br. d, J=13.33 Hz, 1H), 3.92 (s, 3H), 3.42-3.54 (m, 2H), 3.34 (ddd, J=10.88, 6.91, 4.22 Hz, 1H), 2.84 (td, J=13.51, 2.81 Hz, 1H), 2.66 (br. d, J=13.20 Hz, 1H), 1.96 (br. d, J=10.51 Hz, 1H), 1.75-1.90 (m, 1H), 1.33-1.53 (m, 1H), 1.18 (t, J=6.97 Hz, 3H).

Step 3: Synthesis of Methyl 4-((2S,4S)-4-ethoxypiperidin-2-yl)benzoate (Compound of Formula (II), or a Salt Thereof—R=Methyl)

To a 500 mL autoclave which was purged with vacuum/N₂ (S)-C9 in an isopropyl acetate solution (278.4 g, assay 17.96%, 50 g of (S)-C9, 125.80 mmol) and 10% Pd/C (5.0 g, 50% wet) were charged. The reactor was purged with vacuum/H₂ and stirred for 7 hours at 25±5° C. The reaction was followed by HPLC analysis. Filtered the reaction mixture via MCC (7.7 g) which was pre-washed with isopropyl acetate. Rinsed the reactor and MCC with isopropyl acetate (39 g). The mother liquor was combined to afford compound of formula (II) as a light yellow solution (315 g, assay 10.0%, 95.1% yield). ¹H NMR (400 MHz, CDCl₃) δ (ppm)=7.99 (m, J=8.31 Hz, 2H), 7.45 (m, J=8.19 Hz, 2H), 4.09 (dd, J=11.62, 2.20 Hz, 1H), 3.90 (s, 3H), 3.75 (t, J=2.81 Hz, 1H), 3.53 (q, J=6.97 Hz, 2H), 3.17 (td, J=12.13, 2.63 Hz, 1H), 2.91-2.99 (m, 1H), 1.99 (dd, J=13.57, 2.69 Hz, 1H), 1.88 (dt, J=13.79, 2.58 Hz, 1H), 1.69-1.79 (m, 1H), 1.57-1.68 (m, 2H), 1.25 (t, J=7.03 Hz, 3H).

Step 4: Synthesis of the Maleic Salt of Compound of Formula (II) (R=Methyl)

To a 500 mL Radleys Reactor equipped with impeller agitator a solution of methyl 4-((2S,4S)-4-ethoxypiperidin- 2-yl)benzoate (381 g, assay 10.03%, 145.12 mmol, 1.0 eq) from the previous step was charged. The solution was concentrated to 281 g and fresh isopropyl acetate (28.6 g) was added. Then a solution of maleic acid (8.45 g, 72.56 mmol, 0.5 eq) in acetone (30.5 mL) was added at 51±3° C. in 30 minutes. After stirring for 15 minutes, a seed of the maleic salt of compound of formula (II) was added and the mixture was aged for 2 hours. A solution of maleic acid (8.45 g, 72.56 mmol, 0.5 eq) in acetone (30.5 mL) was charged at 51±3° C. in 60 minutes and the mixture was aged for 2 hours. The mixture was cooled to IT=10±3° C. in 6 hours and stirred for 120 minutes. The mixture was filtered and the filter cake was washed with pre-cooled isopropyl acetate (44.4 g). The cake was dried under high vacuum at 55° C. for 5-12 hours to afford maleic salt of compound of formula (II) as white solid (49.8 g, Yield 90.4%). $^1$H NMR (400 MHz, CDCl$_3$) δ (ppm) 9.35-9.78 (m, 2H), 8.02 (m, J=8.31 Hz, 2H), 7.58 (m, J=8.31 Hz, 2H), 6.17 (s, 2H), 4.56 (br. d, J=11.13 Hz, 1H), 3.90 (s, 3H), 3.86 (s, 1H), 3.48-3.57 (m, 2H), 3.38-3.44 (m, 2H), 2.42 (br. t, J=13.57 Hz, 1H), 1.98-2.20 (m, 3H), 1.24 (t, J=6.97 Hz, 3H).

The maleic salt of compound of formula (II) may be characterized by a x-ray powder diffraction pattern (XRPD) comprising four or more 2Θ values (CuKα λ=1.5418 Å) selected from the group consisting of 5.893, 6.209, 11.704, 13.014, 16.403, 17.295, 17.592, 18.629, 18.942, 21.044, 21.733, 21.737, 22.380, 23.528, 24.195, 26.013, 26.825, 29.017, 29.515, 32.250, 35.069, 35.590, and 37.932, measured at a temperature of about 22° C. and an x-ray wavelength, λ, of 1.5418 Å.

Example 7: Synthesis of Tert-butyl 4-formyl-5-methoxy-7-methyl-1H-indole-1-carboxylate (Compound of Formula (III), or a Salt Thereof) According to the Following Sequence

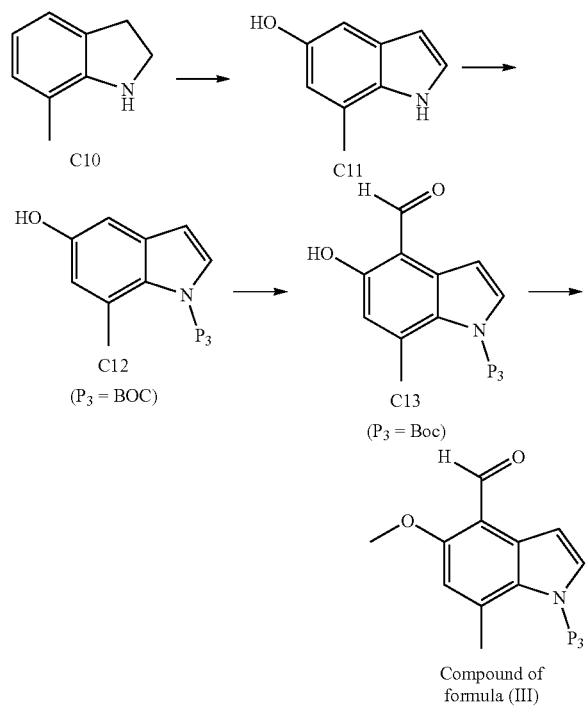

Step 1: Synthesis of 7-methyl-1H-indol-5-ol (C11)

To a 250 mL flask equipped with a thermometer 3.4% Na$_2$HPO$_4$ (100 g, pH=8.91) was charged, followed by addition of Fremy's salt (4.84 g, 2.4 eq). The mixture was stirred at 20±5° C. until a clear solution was formed. A solution of 7-methylindoline in acetone (9.1 g, 11%) was added in one portion. The mixture was stirred at 20±5° C. for 1.5 hours. Then sodium sulfite (0.38 g) was added. The mixture was extracted with ethyl acetate (100 mL×2) The combined organic extracts were dried over anhydrous sodium sulfate, filtered and concentrated. To the residue 20 mL acetonitrile was added. The solution was used directly in the next step.

Step 2: Synthesis of Tert-butyl 5-hydroxy-7-methyl-1H-indole-1-carboxylate (C12, wherein P$_3$=Boc)

The above as prepared solution was cooled to 0±5° C. DMAP (0.34 g, 0.4 eq) was charged followed by addition of (Boc)$_2$O (4.9 g, 3.0 eq). The mixture was warmed to 20±5° C., stirred at 20±5° C. for 30 minutes and concentrated. To the residue was added methanol (40 mL). The mixture was cooled to 0±5° C. Potassium carbonate (5.1 g, 5.0 eq) was added. The mixture was stirred at 0±5° C. for 4 hours, warmed to 20±5° C. and stirred for additional 2 hours. The mixture was cooled to 0±5° C. Acetic acid (2 g) was added. pH was 7-8. The mixture was filtered and the filter cake was washed with methanol (10 mL×2). The filtrate was concentrated and ethyl acetate (30 mL) was added. The mixture was washed with water (20 mL) and 5% brine (20 mL). The organic layer was concentrated to afford a dark oil, which was slurried with (3:2) n-heptane:Ethyl acetate (5 g) to afford a yellow solid. The solid was collected by filtration and dried to give C12 as yellow solid. 27.4% isolate yield from C10. $^1$H-NMR (400 MHz, DMSO-d6): δ (ppm)=9.13 (s, 1H), 7.52 (d, J=3.67 Hz, 1H), 6.74 (d, J=2.2 Hz, 1H), 6.56 (m, 1H), 6.50 (d, J=3.67 Hz, 1H), 2.45 (s, 3H), 1.57 (s, 9H). LCMS (m/z): positive mode 248.1 [M]+, LCMS (m/z): negative mode 246.1 [M-1]–.

Step 3: Synthesis of Tert-butyl 4-formyl-5-hydroxy-7-methyl-1H-indole-1-carboxylate (C13, Wherein P$_3$=Boc)

To a solution of tert-butyl 5-hydroxy-7-methyl-1H-indole-1-carboxylate (C12) (53.8% assay, 1.0 g, 2.2 mmol) in THF (20 mL) was added dropwise the solution of CH$_3$MgBr in THF (1 N, 2.2 mL, 2.2 mmol). The resulting mixture was stirred at 20-25° C. for 10 minutes. (CHO)$_n$ (0.2 g, 6.53 mmol) was added to the mixture. The reaction mixture was heated to 65-70° C. and stirred for 1 hours. The reaction mixture was cooled to 20-25° C. Saturated NH$_4$Cl (20 mL) and MTBE (20 mL) were added. The mixture was separated and the aqueous layer was extracted with MTBE (20 mL). The organic layers were combined and concentrated to give compound C13 as yellow solid (0.7 g, 79% assay, 92% yield). $^1$H-NMR (400 MHz, DMSO-d6) δ (ppm)=10.74 (s, 1H), 10.54 (s, 1H), 7.82 (d, J=4.0 Hz, 1H), 7.34 (d, J=4.0 Hz, 1H), 6.81 (s, 1H), 2.59 (s, 3H), 1.65 (s, 9H). LCMS (m/z): positive mode 290.1 [M]+.

Step 4: Synthesis of Tert-Butyl 4-formyl-5-methoxy-7-methyl-1H-indole-1-carboxylate (Compound of Formula (III))

To a solution of compound C13 (50 mg, 0.182 mmol) in dry DMF (3 mL) was added K$_2$CO$_3$ (50.2 mg, 0.363 mmol).

The mixture was stirred for 10 minutes and then dimethyl sulfate (25.2 mg, 0.20 mmol) was added. The reaction mixture was stirred for 1 hours and poured into ice-water (12 mL). The mixture was filtered and the filter cake was washed with water. The cake was dried under vacuum to give tert-Butyl 4-formyl-5-methoxy-7-methyl-1H-indole-1-carboxylate (Compound of formula (III)) as pale solid (48 mg, 91% yield). $^1$H-NMR (400 MHz, DMSO-d6) δ (ppm)=10.51 (s, 1H), 7.80 (d, J=4.0 Hz, 1H), 7.31 (d, J=4.0 Hz, 1H), 6.81 (s, 1H), 3.95 (s, 3H), 2.61 (s, 3H), 1.59 (s, 9H). LCMS (m/z): negative mode 274.1 [M-1]−.

Example 8: Synthesis of Tert-butyl 4-formyl-5-methoxy-7-methyl-1H-indole-1-carboxylate (Compound of Formula (III), or a Salt Thereof) According to the Following Sequence

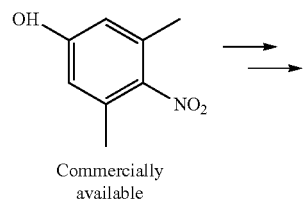

Commercially available

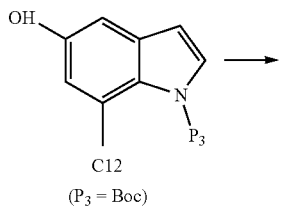

C12
(P$_3$ = Boc)

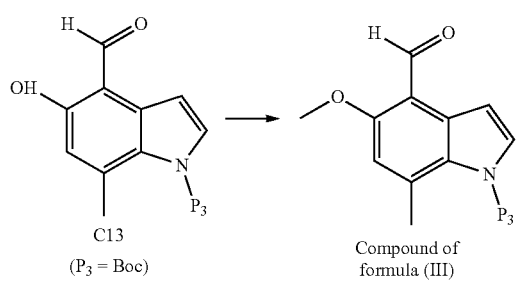

C13
(P$_3$ = Boc)

Compound of formula (III)

Step 1: Synthesis of 5-(benzyloxy)-1,3-dimethyl-2-nitrobenzene

To a solution of commercially available 3,5-dimethyl-4-nitrophenol (100.0 g, 590.4 mmol) in DMF (500 mL), Cs$_2$CO$_3$ (230.8 g, 708.5 mmol) was added and the resulting mixture was stirred for 10 minutes. Then, (bromomethyl)benzene (104.1 g, 590.4 mmol) was added dropwise to the mixture within 30 minutes. The reaction mixture was stirred at 20-25° C. for 1 hour, and then poured into ice-water (1800 mL). The solid separated out was collected by filtration and washed with water (500 mL). The cake was dissolved in ethyl acetate (500 mL) and the solution was washed with a saturated solution of NaCl (50 mL), was separated, and the solution was concentrated to give 5-(benzyloxy)-1,3-dimethyl-2-nitrobenzene 2 (147 g, 97.8% yield) as brown solid. HPLC purity 99.7%. $^1$H-NMR (400 MHz, DMSO-d6) δ (ppm)=7.42 (m, 5H), 6.94 (s, 2H), 5.16 (s, 2H), 2.25 (s, 6H); LCMS (m/z): negative mode 256.2 [M-1]−

Step 2: Synthesis of Tert-butyl 5-hydroxy-7-methyl-1H-indole-1-carboxylate (C12, Wherein P$_3$=Boc)

To a solution of 5-(benzyloxy)-1,3-dimethyl-2-nitrobenzene (60.0 g, 233.2 mmol, from Step 1) in DMF (300 mL) were added DMF-DMA (87.8 g, 699.6 mmol) and pyrrolidine (50.3 g, 699.6 mmol). The solution was heated to 85-90° C. and stirred for 19 hours under nitrogen, then the mixture was cooled to 20-25° C. The volatile components (DMF-DMA, pyrrolidine and DMF) were removed at 65-70° C. on a rotary evaporator. The crude mixture was dissolved in ethyl acetate (300 mL), and Raney Nickel (6.0 g) was added. The reaction mixture was subjected to catalytic hydrogenation under atmospheric pressure, overnight. Then, the reaction mixture was put under nitrogen. The mixture was filtrated and the filtrate was concentrated to provide 5-(benzyloxy)-7-methyl-1H-indole as a black oil. 5-(benzyloxy)-7-methyl-1H-indole was used without further purification into the next step.

5-(benzyloxy)-7-methyl-1H-indole was dissolved in acetonitrile (300 mL), (Boc)$_2$O (53.6 g, 233.2 mmol) and DMAP (5.7 g, 46.6 mmol) were added. The reaction mixture was stirred at 20-25° C. for 1 hour. Acetonitrile was removed on a rotary evaporator, and the residual mixture was dissolved in ethyl acetate (300 mL). The solution was washed with a saturated aqueous solution of NaHCO$_3$ and then concentrated to give a crude oil which was purified by column chromatography (SiO$_2$, 500 g) using a mixture of heptane/MTBE (1:10) to provide the intermediate tert-butyl 5-(benzyloxy)-7-methyl-1H-indole-1-carboxylate as a brown oil (42.1 g, 49.2% yield). HPLC purity 93.5%. $^1$H-NMR (400 MHz, DMSO-d6) δ (ppm)=7.59 (d, J=3.67 Hz, 1H), 7.40 (m, 5H), 7.04 (d, J=2.45 Hz, 1H), 6.81 (d, J=2.2 Hz, 1H), 6.57 (d, J=3.67 Hz, 1H), 5.11 (s, 2H), 2.51 (s, 3H), 1.58 (s, 9H). LCMS (m/z): negative mode 336.2 [M-1]−

To a solution of intermediate tert-butyl 5-(benzyloxy)-7-methyl-1H-indole-1-carboxylate (36.7 g, 100 mmol) in ethanol (250 mL), under nitrogen, 10% Pd/C (10.6 g, 10 mmol) and ammonium formate (6.8 g, 105 mmol) were added. The solution was heated to 45-50° C. and stirred for 5 hours under nitrogen. Then the mixture was cooled to room temperature, filtered, and the filtrate was concentrated to give a residue oil. The residual oil was dissolved in ethyl acetate (250 mL), the solution was washed with a saturated aqueous solution of NaCl (100 mL), the phases were separated. The organic layers were collected and concentrated. The obtained crude mixtures was slurried with a (1:15) mixture of MTBE/Heptane (160 mL) for 2 hours. The precipitate was filtered and washed with heptane (50 mL). The cake was dried under vacuum to give tert-butyl 5-hydroxy-7-methyl-1H-indole-1-carboxylate (C12) as a tawny solid (21.8 g, 87.2% yield). HPLC purity 97.7%. $^1$H-NMR (400 MHz, DMSO-d6) δ (ppm)=9.13 (s, 1H), 7.52 (d, J=3.67 Hz, 1H), 6.74 (d, J=2.2 Hz, 1H), 6.56 (m, 1H), 6.50 (d, J=3.67 Hz, 1H), 2.45 (s, 3H), 1.57 (s, 9H). LCMS (m/z): negative mode 246.2 [M-1]−

Step 3: Synthesis of Tert-butyl 4-formyl-5-hydroxy-7-methyl-1H-indole-1-carboxylate (C13, Wherein P₃=Boc)

To a mixture of MgCl₂ (11.6 g, 119.7 mmol) and (CHO)n (5.0 g, 159.6 mmol), in THF (150 ml), under nitrogen, triethylamine (17.8 mL, 127.7 mmol) was added dropwise and the resulting mixture was stirred at 20-25° C. for 10 minutes. Then, tert-butyl 5-hydroxy-7-methyl-1H-indole-1-carboxylate (C12) (10.0 g, 39.9 mmol) was added to the mixture. The reaction mixture was heated to 65-70° C. and stirred for 3 hours. The reaction mixture was cooled to 20-25° C., followed by addition of 2N HCl (70 ml) and isopropyl acetate (150 ml). The mixture was separated and the organic layer was washed with a 5% NaCl solution. Then, the solution was concentrated to give a crude solid. The solid was slurried with ethanol (100 mL) for 1 hour. The solid precipitate was filtrated, and washed with ethanol (20 mL). The cake was dried under vacuum to give tert-butyl 4-formyl-5-hydroxy-7-methyl-1H-indole-1-carboxylate (C13) as a tawny solid (7.2 g, 63.9% yield). HPLC purity 96.5%. The filtrate solution was concentrated to 20 mL, then stirred for 1 hour. The solid was filtrated, and washed with ethanol (5 mL). The cake was dried by vacuum to give an additional amount of tert-butyl 4-formyl-5-hydroxy-7-methyl-1H-indole-1-carboxylate (C13) as a tawny solid (1.1 g, 95.3% assay, 9.5% yield.). HPLC purity 90.5%. ¹H-NMR (400 MHz, DMSO-d6) δ (ppm)=10.69 (s, 1H), 10.47 (s, 1H), 7.75 (d, J=3.35 Hz, 1H), 7.27 (d, J=3.55 Hz, 1H), 6.74 (s, 1H), 2.51 (s, 3H), 1.59 (s, 9H); LCMS (m/z): negative mode 274.2 [M-1]−.

Step 4: Synthesis of Tert-Butyl 4-formyl-5-methoxy-7-methyl-1H-indole-1-carboxylate (Compound of Formula (III))

To a suspension of tert-butyl 4-formyl-5-hydroxy-7-methyl-1H-indole-1-carboxylate (C13) (6.0 g, 21.3 mmol) in MeCN (60 mL), 50% K₂CO₃ solution (20 mL) and dimethyl sulfate (2.26 mL, 23.4 mmol) were added. The resulting mixture was stirred at 35-40° C. for 3 hours. The reaction mixture was cooled to 20-25° C. and isopropyl acetate (30 mL) was added. The mixture was then extracted; the water layer was extracted with isopropyl acetate (15 mL), the organic layers were combined and concentrated to give a crude residual. The crude residual was dissolved in isopropyl acetate (60 mL), the solution was washed with a statured NH₄Cl solution, and then concentrated to give a crude product (6.6 g). The crude was slurried with ethyl acetate/Heptane (100 mL, 1/50) for 3 hours. The solid was filtrated, washed with heptane (20 mL). The cake was dried under vacuum to give tert-butyl 4-formyl-5-methoxy-7-methyl-1H-indole-1-carboxylate (Compound of formula (III)) as a pink solid (5.5 g, 87.8% yield). HPLC purity 99.3%. ¹H-NMR (400 MHz, DMSO-d6) δ (ppm)=10.52 (s, 1H), 7.79 (d, J=3.67 Hz, 1H), 7.31 (d, J=3.67 Hz, 1H), 7.02 (s, 1H), 3.95 (s, 3H), 2.61 (s, 3H), 1.60 (s, 9H); LCMS (m/z): positive mode 290 [M]+.

Example 9: Synthesis of Compound of Formula (C15), or Salt Thereof (R=Methyl)

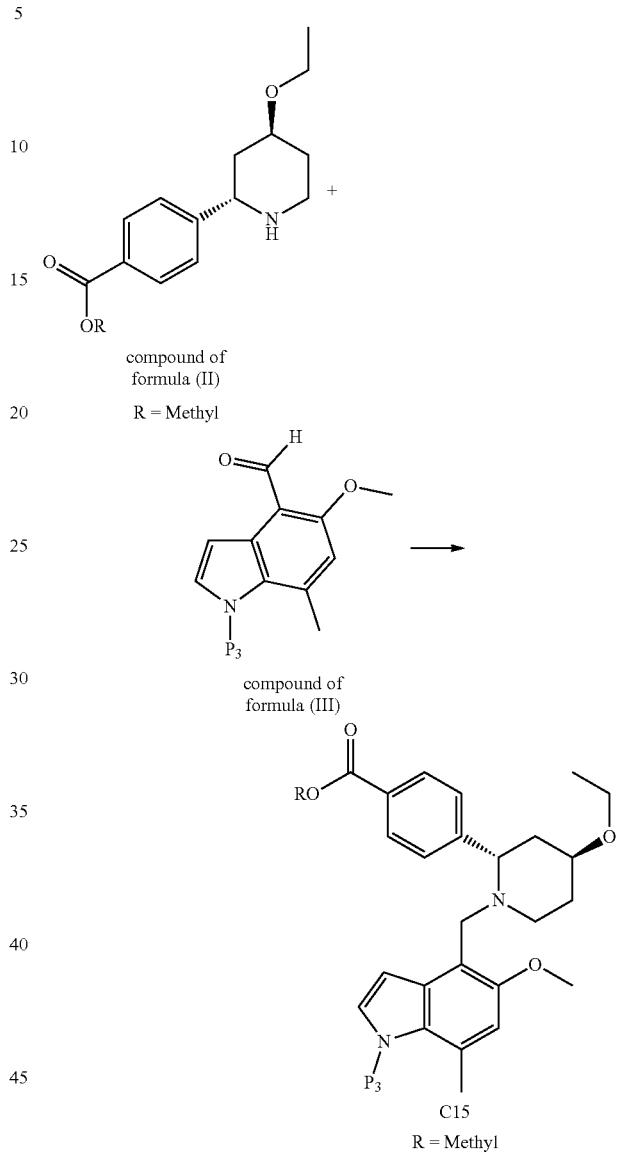

compound of formula (II)

R = Methyl compound of formula (III)

C15

R = Methyl

Method 1 (P₃=Boc and R=methyl): To a vessel were added Ir(CO)₂acac (1 mg, 0.1 mol %), compound of formula (II) (maleic salt, 3 mmol, 1.137 g), compound of formula (III) (3 mmol, 0.867 g) in 9 mL of degassed ethanol. The autoclave was purged 3 times with nitrogen and 3 times with H₂ under stirring (250 RPM). The reactions were run for 24 hours at 75° C. under 20 bar of H₂ at 700 RPM. An aliquot of the reaction was diluted in methanol and was analyzed by HPLC. Compound of formula (C15) was obtained after 24 hours in 88% conversion.

Method 2 (P₃=Boc and R=methyl): To a vessel were added IrCl₃, xH₂O (0.05 mol %, 0.9 mg, anhydrous), compound of formula (II) (maleic salt, 6 mmol, 2.274 g), compound of formula (III) (6 mmol, 1.735 g) in 12 mL of degassed ethanol. The autoclave was purged 3 times with nitrogen and 3 times with carbon monoxide (CO) (250 RPM). The autoclave was pressurized with 1 bar of CO and 19 bar of H₂ and run for 24 hours at 75° C. under 20 bar of H$_2$/CO at 700 RPM. An aliquot of the reaction was diluted in methanol and was analyzed by HPLC. Compound of formula (C15) was obtained after 24 hours in 62% conversion.

$^1$H NMR (400 MHz, DMSO-d$_6$) δ ppm 8.13 (d, J=8.16 Hz, 2H), 7.77 (br. d, J=7.84 Hz, 2H), 7.62-7.68 (m, 1H), 6.85 (s, 1H), 6.80 (d, J=3.76 Hz, 1H), 4.01 (s, 3H), 3.92 (s, 3H), 3.73 (br. s, 1H), 3.55-3.67 (m, 4H), 3.39-3.42 (m, 1H), 2.60-2.70 (m, 5H), 1.99-2.02 (br. d, 1H), 1.82-1.90 (m, 2H), 1.74 (s, 9H), 1.64-1.70 (m, 1H), 1.35 (t, J=6.97 Hz, 3H).

The invention claimed is:

1. A process for preparing a compound of formula (C13),

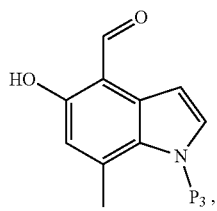

(C13)

or a salt thereof,
wherein P$_3$ is a nitrogen protecting group,
the process comprising the steps of reacting a compound of formula (C12),

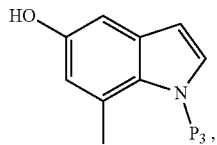

(C12)

or a salt thereof,
wherein P$_3$ is a nitrogen protecting group;
with a Lewis acid or a base, in the presence of an aldehyde source;
to obtain the compound of formula (C13), or a salt thereof.

2. The process of claim 1, wherein the Lewis acid is selected from the group consisting of MgCl$_2$, MgBr$_2$, and MgI$_2$ or mixtures thereof.

3. The process of claim 1, wherein the base is selected from the group consisting of N,N-diisopropylethylamine, 1,8-diazabicyclo[5.4.0]undec-7-ene, 1,4-diazabicyclo[2.2.2]octane, or mixtures thereof.

4. The process of claim 1, wherein the aldehyde source is selected from the group consisting of formaldehyde, paraformaldehyde, and 2,4,6-trimethyl-1,3,5-trioxane.

5. The process of claim 1, wherein P$_3$ is selected from the group consisting of tert-butyloxycarbonyl (Boc), toluenesulfonyl (tosyl), and trifluoromethanesulfonyl.

6. A process for preparing a compound of formula (III),

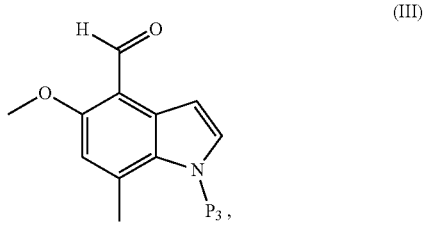

(III)

or a salt thereof,
wherein P$_3$ is a protecting group;
the process comprising the steps of:
(i) reacting a compound of formula (C12)

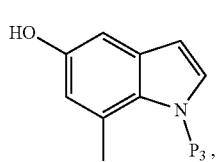

(C12)

or a salt thereof, wherein P$_3$ is a nitrogen protecting group;
with a Lewis acid or a base, in the presence of an aldehyde source, to obtain a compound of formula (C13),

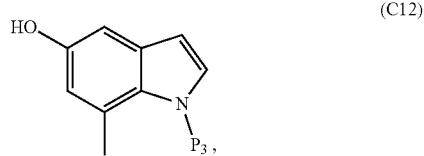

(C13)

wherein P$_3$ is a nitrogen protecting group, and
(ii) reacting the compound of formula (C13), or a salt thereof, with an inorganic base, in the presence of a methylating agent,
to obtain the compound of formula (III), or a salt thereof.

7. The process of claim 6, wherein the Lewis acid is selected from the group consisting of MgCl$_2$, MgBr$_2$, and MgI$_2$ or mixtures thereof.

8. The process of claim 6, wherein the base is selected from the group consisting of N,N-diisopropylethylamine, 1,8-diazabicyclo[5.4.0]undec-7-ene, 1,4-diazabicyclo[2.2.2]octane, or mixtures thereof.

9. The process of claim 6, wherein the aldehyde source is selected from the group consisting of formaldehyde, paraformaldehyde, and 2,4,6-trimethyl-1,3,5-trioxane.

10. The process of claim 6, wherein P$_3$ is selected from the group consisting of tert-butyloxycarbonyl (Boc), toluenesulfonyl (tosyl), and trifluoromethanesulfonyl.

* * * * *